US008945621B2

(12) United States Patent
Ault et al.

(10) Patent No.: US 8,945,621 B2
(45) Date of Patent: Feb. 3, 2015

(54) METHOD FOR TREATING A PATIENT AT RISK FOR DEVELOPING AN NSAID-ASSOCIATED ULCER

(75) Inventors: Brian Ault, Wilmington, DE (US); Clara Hwang, Wilmington, DE (US); Everardus Orlemans, Chapel Hill, NC (US); John R Plachetka, Chapel Hill, NC (US); Mark Sostek, Wilmington, DE (US)

(73) Assignees: Pozen Inc., Chapel Hill, NC (US); Horizon Pharma USA, Inc., Deerfield, IL (US)

( * ) Notice: Subject to any disclaimer, the term of this patent is extended or adjusted under 35 U.S.C. 154(b) by 480 days.

(21) Appl. No.: 12/822,612

(22) Filed: Jun. 24, 2010

(65) Prior Publication Data

US 2010/0330179 A1 Dec. 30, 2010

Related U.S. Application Data

(60) Provisional application No. 61/220,420, filed on Jun. 25, 2009, provisional application No. 61/225,970, filed on Jul. 16, 2009, provisional application No. 61/310,525, filed on Mar. 4, 2010.

(51) Int. Cl.
*A61K 9/24* (2006.01)
*A61K 31/192* (2006.01)
*A61K 31/4439* (2006.01)
*A61K 45/06* (2006.01)

(52) U.S. Cl.
CPC .............. *A61K 31/192* (2013.01); *A61K 9/209* (2013.01); *A61K 31/4439* (2013.01); *A61K 45/06* (2013.01)
USPC ...................................................... 424/472

(58) Field of Classification Search
USPC ........................................................ 424/472
See application file for complete search history.

(56) References Cited

U.S. PATENT DOCUMENTS

| | | |
|---|---|---|
| 4,198,390 A | 4/1980 | Rider |
| 4,255,431 A | 3/1981 | Junggren et al. |
| 4,344,929 A | 8/1982 | Bonsen et al. |
| 4,508,905 A | 4/1985 | Junggren et al. |
| 4,554,276 A | 11/1985 | LaMattina |
| 4,562,261 A | 12/1985 | Hirata et al. |
| 4,619,934 A | 10/1986 | Sunshine et al. |
| 4,676,984 A | 6/1987 | Wu et al. |
| 4,704,278 A | 11/1987 | Wu et al. |
| 4,726,951 A | 2/1988 | Panoz et al. |
| 4,738,974 A | 4/1988 | Brandstrom |
| 4,757,060 A | 7/1988 | Lukacsko et al. |
| 4,758,579 A | 7/1988 | Kohl et al. |
| 4,766,117 A | 8/1988 | Crawford et al. |
| 4,786,505 A | 11/1988 | Lovgren et al. |
| 4,853,230 A | 8/1989 | Lovgren et al. |
| 4,865,847 A | 9/1989 | Gosswein |
| 4,948,581 A | 8/1990 | Sawayanagi et al. |
| 4,965,065 A | 10/1990 | Lukacsko et al. |
| 5,026,560 A | 6/1991 | Makino et al. |
| 5,035,899 A | 7/1991 | Saeki et al. |
| 5,037,815 A | 8/1991 | Lukacsko et al. |
| 5,043,358 A | 8/1991 | Lukacsko et al. |
| 5,051,262 A | 9/1991 | Panoz et al. |
| 5,093,132 A | 3/1992 | Makino et al. |
| 5,204,118 A | 4/1993 | Goldman et al. |
| 5,260,333 A | 11/1993 | Lukacsko et al. |
| 5,364,616 A | 11/1994 | Singer et al. |
| 5,373,022 A | 12/1994 | Fawzi et al. |
| 5,409,709 A | 4/1995 | Ozawa et al. |
| 5,417,980 A | 5/1995 | Goldman et al. |
| 5,466,436 A | 11/1995 | Stables |
| 5,514,663 A | 5/1996 | Mandel |
| 5,601,843 A | 2/1997 | Gimet et al. |
| 5,631,022 A | 5/1997 | Mandel et al. |
| 5,643,960 A | 7/1997 | Breitner et al. |
| 5,667,802 A | 9/1997 | Grimberg |
| 5,679,376 A | 10/1997 | Stevens et al. |
| 5,686,105 A | 11/1997 | Kelm et al. |
| 5,690,960 A | 11/1997 | Bengtsson et al. ............ 424/480 |
| 5,702,723 A | 12/1997 | Griffin |
| 5,714,504 A | 2/1998 | Lindberg et al. |
| 5,716,648 A | 2/1998 | Halskov et al. |
| 5,750,531 A | 5/1998 | Lee et al. |
| 5,817,338 A | 10/1998 | Bergstrand et al. |
| 5,817,340 A | 10/1998 | Roche et al. |

(Continued)

FOREIGN PATENT DOCUMENTS

| | | |
|---|---|---|
| AU | 2006235929 | 11/2006 |
| CA | 2139653 | 12/1994 |

(Continued)

OTHER PUBLICATIONS

Abelo et al., "Pharmacodynamic modeling of reversible gastric acid pump inhibition in dog and man," European Journal of Pharmaceutical Sciences, 14, pp. 339-346 (2001).

Alexander, et al., "Pilot Evaluation of a Novel Combination Tablet (PN 400) Containing a Proton Pump Inhibitor and a Nonsteroidal Anti-Inflammatory Drug in Prevention of Upper Gastrointestinal Mucosal Injury," American Journal of Gastroenterology, 100(9), p. S68, 135 (2005).

Andersson, "Pharmacokinetics, metabolism and interactions of acid pump inhibitors," Clin. Pharmacokinet. 31(1)9-28 (Jul. 1996).

Anonymous: "A 12-month, phase 3, open-label, multi-center study to evaluate the long-term safety of PN 400" Internet article (Sep. 11, 2007), XP002553437, retrieved from the internet, URL:http://clinicaltrials.gov/show/NCT00527904>.

(Continued)

Primary Examiner — Adam C Milligan
(74) Attorney, Agent, or Firm — Parker Highlander PLLC

(57) ABSTRACT

The present disclosure is directed to a method for treating a disease or disorder in a patient at risk of developing an NSAID-associated ulcer by administering to said patient in need thereof a pharmaceutical composition in unit dose form comprising naproxen, or pharmaceutically acceptable salt thereof, and esomeprazole, or pharmaceutically acceptable salt thereof to said at risk patient and thereby decreasing the patient's risk of developing an ulcer.

16 Claims, No Drawings

(56) References Cited

U.S. PATENT DOCUMENTS

| | | | |
|---|---|---|---|
| 5,840,737 A | 11/1998 | Phillips | |
| 5,872,145 A | 2/1999 | Plachetka | 514/415 |
| 5,900,424 A | 5/1999 | Kallstrom et al. | |
| 5,955,451 A | 9/1999 | Lichtenberger et al. | |
| 6,013,281 A | 1/2000 | Lundberg et al. | |
| 6,025,395 A | 2/2000 | Breitner et al. | |
| 6,060,499 A | 5/2000 | Plachetka | 514/415 |
| 6,093,734 A | 7/2000 | Garst et al. | |
| 6,126,816 A | 10/2000 | Ruiz, Jr. | 210/95 |
| 6,132,768 A | 10/2000 | Sachs et al. | |
| 6,132,771 A | 10/2000 | Depui et al. | |
| 6,136,344 A | 10/2000 | Depui et al. | |
| 6,160,020 A | 12/2000 | Ohannesian et al. | |
| 6,162,816 A | 12/2000 | Bohlin et al. | |
| 6,183,776 B1 | 2/2001 | Depui et al. | |
| 6,183,779 B1 | 2/2001 | Ouali et al. | |
| 6,207,188 B1 | 3/2001 | Gustavsson et al. | |
| 6,231,888 B1 | 5/2001 | Lerner et al. | |
| 6,287,600 B1 | 9/2001 | Ouali et al. | |
| 6,365,184 B1 | 4/2002 | Depui et al. | |
| 6,369,085 B1 | 4/2002 | Cotton et al. | |
| 6,372,255 B1 | 4/2002 | Saslawski et al. | |
| 6,387,410 B1 | 5/2002 | Woolfe et al. | |
| 6,395,298 B1 | 5/2002 | Flanagan et al. | |
| 6,428,810 B1 | 8/2002 | Bergstrand et al. | |
| 6,485,747 B1 | 11/2002 | Flanagan et al. | |
| 6,489,346 B1 | 12/2002 | Phillips | |
| 6,544,556 B1 | 4/2003 | Chen et al. | |
| 6,599,529 B1 | 7/2003 | Skinhoj et al. | |
| 6,610,323 B1 | 8/2003 | Lundberg et al. | |
| 6,613,354 B2 | 9/2003 | Depui et al. | |
| 6,632,451 B2 | 10/2003 | Penhasi et al. | |
| 6,641,838 B2 | 11/2003 | Pather et al. | |
| 6,645,988 B2 | 11/2003 | Phillips | |
| 6,673,819 B2 | 1/2004 | Bergman et al. | |
| 6,685,964 B1 | 2/2004 | Bartholomaeus et al. | |
| 6,699,885 B2 | 3/2004 | Phillips | |
| 6,713,089 B1 | 3/2004 | Bertelsen et al. | |
| 6,749,867 B2 | 6/2004 | Robinson et al. | |
| 6,780,882 B2 | 8/2004 | Phillips | |
| 6,787,164 B2 | 9/2004 | Gelber et al. | |
| 6,797,283 B1 | 9/2004 | Edgren et al. | |
| 6,869,615 B2 | 3/2005 | Chen et al. | |
| 6,875,872 B1 | 4/2005 | Lindberg et al. | |
| 6,926,907 B2 | 8/2005 | Plachetka | |
| 7,029,701 B2 | 4/2006 | Chen | |
| 7,030,162 B2 | 4/2006 | Plachetka et al. | 514/619 |
| 7,060,694 B2 | 6/2006 | Plachetka et al. | 514/177 |
| 7,094,425 B2 | 8/2006 | Scott et al. | |
| 7,332,183 B2 | 2/2008 | Plachetka et al. | 424/472 |
| 7,399,772 B2 | 7/2008 | Phillips | |
| 7,411,070 B2 | 8/2008 | Cotton et al. | |
| 7,488,497 B2 | 2/2009 | Depui et al. | |
| 7,745,466 B2 | 6/2010 | Cotton et al. | |
| 7,785,626 B2 | 8/2010 | Pettersson et al. | |
| 7,846,914 B2 | 12/2010 | Petrus | |
| 8,206,741 B2 | 6/2012 | Plachetka | |
| 2001/0025107 A1 | 9/2001 | Barberich et al. | |
| 2001/0036473 A1 | 11/2001 | Scott et al. | 424/463 |
| 2001/0044410 A1 | 11/2001 | Gelber et al. | 514/27 |
| 2002/0012676 A1 | 1/2002 | Lundberg et al. | |
| 2002/0042433 A1 | 4/2002 | Yelle et al. | |
| 2002/0044962 A1 | 4/2002 | Cherukuri et al. | |
| 2002/0045184 A1 | 4/2002 | Chen | |
| 2002/0086029 A1 | 7/2002 | Lundberg et al. | |
| 2002/0090395 A1 | 7/2002 | Woolfe et al. | |
| 2002/0111370 A1 | 8/2002 | Bergman et al. | 514/338 |
| 2002/0155153 A1 | 10/2002 | Depui et al. | 424/452 |
| 2002/0160046 A1 | 10/2002 | Robinson et al. | 424/469 |
| 2003/0008903 A1 | 1/2003 | Barberich et al. | |
| 2003/0040537 A1 | 2/2003 | Plachetka et al. | 514/406 |
| 2003/0113375 A1 | 6/2003 | Lundberg et al. | |
| 2003/0129235 A1 | 7/2003 | Chen et al. | 424/470 |
| 2003/0215527 A1 | 11/2003 | Phillips | |
| 2003/0232080 A1 | 12/2003 | Pather et al. | |
| 2003/0232876 A1 | 12/2003 | Plachetka | 514/419 |
| 2004/0022846 A1 | 2/2004 | Depui et al. | 424/452 |
| 2004/0048896 A1 | 3/2004 | Phillips | |
| 2004/0121004 A1 | 6/2004 | Taneja | |
| 2004/0131676 A1 | 7/2004 | Taneja | |
| 2004/0171646 A1 | 9/2004 | Phillips | |
| 2004/0180089 A1 | 9/2004 | Plachetka et al. | 424/4 |
| 2005/0004171 A1 | 1/2005 | Phillips | |
| 2005/0042304 A1 | 2/2005 | Phillips | |
| 2005/0054682 A1 | 3/2005 | Phillips | |
| 2005/0147668 A1 | 7/2005 | Bertelsen et al. | |
| 2005/0163847 A1 | 7/2005 | Cheng et al. | |
| 2005/0227949 A1 | 10/2005 | Edaltpour | |
| 2005/0249806 A1 | 11/2005 | Proehl et al. | |
| 2005/0249811 A1 | 11/2005 | Plachetka | 424/472 |
| 2006/0165797 A1 | 7/2006 | Plachetka | |
| 2006/0177504 A1 | 8/2006 | Sundharadas | 424/488 |
| 2006/0178348 A1 | 8/2006 | Plachetka | |
| 2006/0178349 A1 | 8/2006 | Plachetka | |
| 2006/0287284 A1 | 12/2006 | Schutze et al. | |
| 2007/0122470 A1 | 5/2007 | Johansson et al. | |
| 2007/0154542 A1 | 7/2007 | Tananbaum et al. | |
| 2007/0184078 A1 | 8/2007 | Chen | |
| 2007/0207200 A1 | 9/2007 | Plachetka et al. | 424/451 |
| 2007/0237820 A1 | 10/2007 | Cheng et al. | |
| 2007/0243251 A1 | 10/2007 | Taneja | |
| 2008/0031941 A1 | 2/2008 | Pettersson | |
| 2008/0031950 A1 | 2/2008 | Sesha | |
| 2008/0103169 A1 | 5/2008 | Phillips | |
| 2009/0074863 A1 | 3/2009 | Taneja | |
| 2009/0075950 A1 | 3/2009 | Taneja | |
| 2009/0297594 A1 | 12/2009 | Depui et al. | 424/451 |
| 2010/0062064 A1 | 3/2010 | Ault et al. | |
| 2010/0172983 A1 | 7/2010 | Plachetka | |
| 2010/0178334 A1 | 7/2010 | Johansson et al. | |
| 2012/0064156 A1 | 3/2012 | Plachetka | |

FOREIGN PATENT DOCUMENTS

| | | |
|---|---|---|
| DE | 4035455 | 5/1992 |
| DE | 19801811 | 12/2004 |
| EP | 0 005 129 A1 | 10/1979 |
| EP | 0005129 | 4/1981 |
| EP | 0 124 495 A2 | 11/1984 |
| EP | 0 166 287 A1 | 1/1986 |
| EP | 0 167 958 A2 | 1/1986 |
| EP | 0 174 726 A1 | 3/1986 |
| EP | 0124495 | 1/1987 |
| EP | 0 244 380 A2 | 11/1987 |
| EP | 0 244 380 B1 | 11/1987 |
| EP | 0174726 | 4/1989 |
| EP | 0320550 | 6/1989 |
| EP | 0320551 | 6/1989 |
| EP | 0166287 | 8/1989 |
| EP | 0167958 | 1/1991 |
| EP | 0 426 479 A1 | 5/1991 |
| EP | 0244380 | 1/1993 |
| EP | 0 550 083 A1 | 7/1993 |
| EP | 0426479 | 2/1994 |
| EP | 0550083 | 3/1999 |
| EP | 1 020 461 A2 | 7/2000 |
| EP | 1 068 867 A2 | 1/2001 |
| EP | 1068867 | 9/2003 |
| EP | 1726300 | 11/2006 |
| EP | 1726301 | 11/2006 |
| EP | 1020461 | 7/2009 |
| GB | 2105193 | 3/1983 |
| GB | 2163747 | 3/1986 |
| GB | 2216413 | 10/1989 |
| JP | 2005-145894 | 6/2005 |
| WO | 8503443 | 8/1985 |
| WO | 9006925 | 6/1990 |
| WO | 9116886 | 11/1991 |
| WO | 9116895 | 11/1991 |
| WO | 9116896 | 11/1991 |
| WO | 9119711 | 12/1991 |
| WO | 9119712 | 12/1991 |
| WO | 9311750 | 6/1993 |
| WO | 9312817 | 7/1993 |

(56) References Cited

FOREIGN PATENT DOCUMENTS

| WO | 9407541 | 4/1994 |
|---|---|---|
| WO | 9427988 | 12/1994 |
| WO | 9501977 | 1/1995 |
| WO | 9532959 | 12/1995 |
| WO | 9605177 | 2/1996 |
| WO | 9605199 | 2/1996 |
| WO | 9614839 | 5/1996 |
| WO | 9622780 | 8/1996 |
| WO | 9711701 | 4/1997 |
| WO | 9725064 | 7/1997 |
| WO | 9813073 | 4/1998 |
| WO | 9822117 | 5/1998 |
| WO | 9822118 | 5/1998 |
| WO | 9854171 | 12/1998 |
| WO | 9900380 | 1/1999 |
| WO | 9912524 | 3/1999 |
| WO | 9929320 | 6/1999 |
| WO | 9966919 | 12/1999 |
| WO | 0001368 | 1/2000 |
| WO | 0015195 | 3/2000 |
| WO | 0056339 | 9/2000 |
| WO | 0071122 | 11/2000 |
| WO | 0072838 | 12/2000 |
| WO | 0078293 | 12/2000 |
| WO | 0124777 | 4/2001 |
| WO | 0166088 | 9/2001 |
| WO | 0222108 | 3/2002 |
| WO | 02066002 | 8/2002 |
| WO | WO 02/098352 | 12/2002 |
| WO | 03017980 | 3/2003 |
| WO | 2004062552 | 7/2004 |
| WO | 2004064815 | 8/2004 |
| WO | 2005074536 | 8/2005 |
| WO | 2005074930 | 8/2005 |
| WO | 2006044202 | 4/2006 |
| WO | 2007064274 | 6/2007 |
| WO | 2007078874 | 7/2007 |
| WO | 2008101060 | 8/2008 |
| WO | 2009012393 | 1/2009 |
| WO | 2009145905 | 12/2009 |
| WO | 2010151697 | 12/2010 |

OTHER PUBLICATIONS

Anonymous: "PK Study to evaluate Esomeprazole plasma levels following the administration of PN 400" Internet article (Feb. 11, 2008), XP002553435, retrieved from the internet: URL:http://clinicaltrials.gov/show/NCT00599404>.
Anonymous: "Study evaluating the bioavailability of Naproxen 500 mg in three formulations," Internet article (May 11, 2008), XP002553436m retrieved from the internet: URL:http://clinicaltrials.gov/show/NCT00665743>.
Arthrotec Data sheet (Aug. 2009).
Awtry, et al., "Aspirin," Circulation 101:1206-1218 (2000).
Ballinger, et al., "COX-2 Inhibitors vs. NSAIDs in Gastrointestinal Damage and Prevention," Exp. Opin. Pharmacother. 2(1):31-40 (2001).
Barnett et al., "Effects of SCH 32651 on resting and stimulated acid secretion in guinea-pig isolated fundic mucosa," Br. J. Pharmac., 83, pp. 75-82 (1984).
Berardi et al., "Elevation of Gastric pH with Ranitidine does not affect the release characteristics of sustained release Ibuprofen tablets," Biopharmaceutics & Drug Disposition, 9: pp. 337-347 (1988).
Bergmann et al., "Protection against aspirin-induced gastric lesions by lansoprazole: simultaneous evaluation of functional and morphologic responses," Clin. Pharmcol. Ther., 52, pp. 413-416 (Oct. 1992).
Bianchi Porro et al., "Pantoprazole vs placebo in prevention of NSAID-induced ulcers," Gastroenterology, 114(4), p. A74 (1998).
Bianchi Porro, et al., "Prevention of gastroduodenal damage with omeprazole in patients receiving continuous NSAIDs treatment. A double blind placebo controlled study," Ital. J. Gastroenterol. Hepatol., 30, pp. 43-47 (1998).
Bianchi Porro, et al., "Why Are Non-Steroidal Anti-Inflammatory Drugs Important in Peptic Ulcers?" Aliment. Pharmacol. Therap, 1, pp. 540S-547S (1987).
Bigard English translation—Bigard, et al. "Effet protecteur de l'omeprazole sur les lesions gastriques induites par une prise unique d'aspirine chez l'homme," Gastroenterol. Clin. Biol., 12, pp. 770-771 (1998).
Bigard et al., "Complete prevention by omeprazole of aspirin induced gastric lesions in healthy subjects," Gut, 29(5), p. A712, T49 (1988).
Bigard et al., "Effet protecteur de l'omeprazole sur les lesions gatriques induites par une prise unique d'aspirine chez l'homme," Gastroenterol. Clin. Biol., 12, pp. 770-771 (1998).
Bombardier et al., "Comparison of upper gastrointestinal toxicity of rofecoxib and naproxen in patients with rheumatoid arthritis," N. Engl. J. Med., 343, pp. 1520-1528 (2000).
Brown et al., "Prevention of the gastrointestinal adverse effects of nonsteroidal anti-inflammatory drugs," Pract. Drug Safety, 21, pp. 503-512 (1999).
Brown, et al., "Asprin- and Indomethacin-Induced Ulcers and Their Antagonism by Antihistamines," Euro. J. Pharm., 51, pp. 275-283 (1978).
Byrn et al., "Pharmaceutical solids: A strategic approach to regulatory considerations," Pharm. Res., 12(7), pp. 945-954 (1995).
Carrasco-Portugal, et al., "Bioavailability of a Formulation Containing a Diclofenac-Ranitidine Combination," Proc. West. Pharmacol. Soc., 45, pp. 8-10 (2002).
Chan et al., "Eradication of H. pylori versus maintenance acid suppression to prevent recurrent ulcer hemorrhage in high risk NSAID users: A prospective randomized study," Gastroenterology, 114, p. A87, G0356 (1998).
Chan, et al., "Clopidogrel versus Aspirin and Esomeprazole to prevent recurrent ulcer bleeding," New Eng. J. Med. 352, pp. 238-244 (2005).
Chandrarnouli et al., J. Pharmaceutical Pain and Symptom Control, pp. 27-40 (2000).
Chang et al., "Polymetharcrylates," Handbook of Pharmaceutical Excipients, Fifth Edition, Ed. Raymond C. Rowe, Paul J. Sheskey and Sian C. Owen, London: Pharmaceutical Press, pp. 553-560 (2006).
Cullen et al., "Primary gastroduodenal prophylaxis with omeprazole for non-steroidal anti-inflammatory drug users," Aliment. Pharmacol. Ther., 12, pp. 135-140 (1998).
Dajani, Esam Z., "Perspective on the Gastric Antisecretory Effects of Misoprostol in Man," Prostaglandins, 33, pp. 68-77 (1987).
Daneshmend et al., "Abolition by omeprazole of aspirin-induced gastric mucosal injury in man," Gut, 31, pp. 514-517 (1990).
Daneshmend et al., "Use of microbleeding and an ultrathin endoscope to assess gastric mucosal protection by Famotidine," Gastroenterology, 97, pp. 944-949 (1989).
Dent et al., "Why proton pump inhibition should heal and protect against nonsteroidal anti-inflammatory drug ulcers," Am. J. Med., 104, pp. 52S-55S (1998).
Ehsanullah et al, "Prevention of gastroduodenal damage induced by non-steroidal anti-inflammatory drugs: controlled trial of ranitidine," BMJ, 297, pp. 1017-1021 (Oct. 1988).
Ekstrom et al., "Prevention of peptic ulcer and dyspeptic symptoms with omeprazole in patients receiving continuous non-steroidal anti-inflammatory drug therapy," Scand. J. Gastroenterol., 31, pp. 753-758 (1996).
Ene et al., "A study of the inhibitory effects of SCH 28080 on gastric secretion in man," Br. J. Pharmac., 76, pp. 389-391 (1982).
Erlandsson et al., "Resolution of the enantiomers of omeprazole and some of its analogues by liquid chromatography on a trisphenycarbamoylcellulose-based stationary phase," J. Chromatog., 532, pp. 305-319 (1990).
Feldman et al., "Effect on antacid on absorption on enteric-coated aspirin," JAMA, 227(6), pp. 660-661 (1974).
Florence et al., "Novel oral drug formulations their potential in modulating adverse effects," Drug Safety, 10(3), pp. 233-266 (1994).
Frank, et al., "Reduction of Indomethacin Induced Gastrduodenal Mucosal Injury and Gastro-intestinal Symptoms with Cimetidine in Normal Subjects," J. Rheum., 16, pp. 1249-1252 (1989).

(56) References Cited

OTHER PUBLICATIONS

Gengo, et al., "Prevalence of Platelet Nonresponsiveness to Aspirin in Patients Treated for Secondary Stroke Prophylaxis and in Patients With Recurrent Ischemic Events," J. Clin. Pharmacol., 48, pp. 335-343 (2008).
Goldstein et al., "116 a single tablet multilayer formulation of enteric-coated naproxen coupled with non-enteric-coated omeprazole is associated with a significantly reduced incidence of gastric ulcers vs. enteric-coated naproxen: A prospective, randomized, double-blind study," Gastroenterology, Elsevier, Philadelphia, PA, 134(4), p. A-19 (Apr. 1, 2008).
Goldstein, et al., "PN400 Significantly Improves Upper Gastrointestinal Tolerability Compared with Enteric-Coated Naproxen Alone in Patients Requiring Chronic NSAID Therapy: Results from Two Prospective, Randomized, Controlled Trials," POZEN Inc. sponsored study, 74th Annual Scientific Meeting of the American College of Gastroenterology, San Diego, CA (Oct. 27, 2009).
Goldstein, et al., "PN400 Significantly Reduces the Incidence of Gastric Ulcers Compared With Enteric-Coated Naproxen in Patients Requiring Chronic NSAID Therapy Regardless of Low-Dose Aspirin Use: Results from Two Prospective, Randomized Controlled Trials," POZEN Inc. sponsored study, ACR/ARHP Mtg, (Oct. 16-21, 2009).
Graham, et al., "Duodenal and Gastric Ulcer Prevention with Misoprostol in Arthritis Patients Taking NSAIDs," Ann. Intern. Med. 119(4):257-262 (Aug. 1993).
Grosser et al., "Thromboxane Generation," in Platelets, Alan Michelson ed., Elseiver Science, pp. 565-574 (2007).
Gurbel et al., "Abstract 4267: PA32520 (Single-tablet of enteric coated aspirin 325 mg + immediate-release omeprazole 20 mg): Aspirin therapy combining greater thromboxane supression and lower upper gastrointestinal damage.", Circulation, 118, p. S855 (2008).
Hart, et al., "Aspirin Dosage and Thromboxane Synthesis in Patients with Vascular Disease," Pharmacotherapy 23(5):579-584 (2003).
Hassan-Alin et al., "11651 lack of drug-drug interaction between esomeprazole and naproxen in healthy subjects," Gastroenterology, 124(4), Supp. 1, p. A541 (Apr. 2003).
Hawkey et al., "Omeprazole compared with misoprostol for ulcers associated with nonsteroidal anti-inflammatory drugs," N. Engl. J. Med., 338, pp. 727-734 (1998).
Hawkey et al., "Progress in prophylaxis against nonsteroidal anti-inflammatory drug-associated ulcers and erosions," Am. J. Med., 104, pp. 67S-74S (1998).
Office Action dated Jan. 5, 2012 issued for US Pub No. 2010/0062064.
Office Action dated Jul. 30, 2012 issued for US Pub No. 2010/0062064.
Office Action dated Apr. 22, 2004 issued for US Patent No. 6,926,907.
Office Action dated Oct. 10, 2004 issued for US Patent No. 6,926,907.
Notice of Allowance dated Mar. 29, 2005 issued for US Patent No. 6,926,907.
Office Action dated Mar. 30, 2009 issued for US Patent No. 8,206,741.
Office Action dated Nov. 19, 2009 issued for US Patent No. 8,206,741.
Office Action dated Oct. 25, 2010 issued for US Patent No. 8,206,741.
Office Action dated Jun. 16, 2011 issued for US Patent No. 8,206,741.
Interview Summary dated Nov. 15, 2011 issued for US Patent No. 8,206,741.
Interview Summary dated Mar. 7, 2012 issued for US Patent No. 8,206,741.
Interview Summary dated Apr. 19, 2012 issued for US Patent No. 8,206,741.
Notice of Allowance dated May 13, 2012 issued for US Patent No. 8,206,741.
IPER issued for WO 2010/151216, Jan. 4, 2012.
ISR issued for WO 2010/151216, Sep. 20, 2010.
Supplemental ISR issued for WO 2010/151216, Oct. 20, 2011.
Written Opinion issued for WO 2010/151216, Sep. 20, 2010.
U.S. Appl. No. 13/475,446, filed May 18, 2012.
Preliminary Amendment for U.S. Appl. No. 13/475,446, filed May 18, 2012.
Panara et al., "Effects of the novel anti-inflammatory compounds, N[2-(cyclohexyloxy)-4-nitrophenyl] methanesulphonamide (NS-398) and 5-methanesulphonamido-6-(2,4-difluorothio-phenyl)-1-inda none (L-745,337), on the cyclo-oxygenase activity of human blood prostaglandin endoperoxide synthases," British Journal of Pharmacology, 116, pp. 2429-2434 (1995).
Pang et al., "Modeling of intestinal drug absorption: roles of transporters and metabolic enzymes (for the Gillette review series)" Drug Metabolism and Disposition, 31(12), pp. 1507-1519 (2003).
Patrono, et al., "Low-Dose Aspirin for the Prevention of Atherothrombosis," New Eng. J. Med., 353, pp. 2373-2383 (2005).
Petersen, "Doubts are raised on the safety of 2 popular arthritis drugs," NY Times, p. C1 (May 22, 2001).
Pilbrant et al., "Development of an Oral Formulation of Omeprazole," Scand. J. Gastroenterol., 20, Supp. 108, pp. 113-120 (1985).
Pirmohamed et al., "Adverse drug reactions as cause of admission to hospital: prospective analysis of 18,820 patients," Br. Med. J., 329, pp. 15-19 (2004).
Porter S.C., "Coating of Pharmaceutical Dosage Forms," in: A. Gennaro (Ed.), Remington: the Science and Practice of Pharmacy, 19th ed., pp. 1650-1651 (1995).
Qureshi, et al., "Pharmacokinetics of Two Enteric-Coated Ketoprofen Products in Humans with or Coadministration of Omeprazole and Comparison with Dissolution Findings," Pharmaceutical Research, 11(11), pp. 1669-1672 (1994).
Raskin, et al., "Misoprostol Dosage in the Prevention of Nonsteroidal Anti-Inflammatory Drug-Induced Gastric and Duodenal Ulcers: A Comparison of Three Regimens," Ann. Intern. Med., 123(5), pp. 344-350 (Sep. 1995).
Richardson et al., "Proton pump inhibitors, pharmacology and rationale for use in gastrointestinal disorders," Drugs, 56 (3), pp. 307-335 (1998).
Robinson, et al., "Effects of Ranitidine Gastroduodenal Mucosal Damage Induced by Nonsteroidal Anti-inflammatory Drugs," Dig. Dis. Sci., 34(3), pp. 424-428 (Mar. 1989).
Roth, et al., "Cimetidine Therapy in Nonsteroidal Anti-inflammatory Drug Gastropathy: Double-blind Long-term Evaluation," Arch. Intern. Med., 147, pp. 1798-1801 (1987).
Rubinstein, "Gastrointestinal anatomy physiology and permeation pathways," Enhancement in Drug Discovery, CRC Press, pp. 3-35 (2007).
Sangiah et al., "Effects of misoprostol and omeprazole on basal gastric pH and free acid content in horses," Res. Vet. Sci., 47(3), pp. 350-354 (1989).
Savarino et al., "Effect of one-month treatment with nonsteroidal anti-inflammatory drugs (NSAIDs) on gastric pH of rheumatoid arthritis patients," Digestive Diseases and Sciences, 43, pp. 459-463 (1998).
Scarpignato et al., Gastroenterology International; pp. 186-215 (1999).
Scheiman et al., "NSAID-induced peptic ulcer disease: a critical review of pathogenesis and management," Dig. Dis., 12, pp. 210-222 (1994).
Scheiman et al., "Omeprazole ameliorates aspirin-induced gastroduondenal injury," Digestive Diseases and Sciences, 39(1), pp. 97-103 (1994).
Scheiman, Seminars in Arthritis and Rheumatism, pp. 201-210 (1992).
Scott and Sundell, "Inhibition of H+K+ ATPase by SCH 28080 and SCH 32651," European Journal of Pharmacology, 112, pp. 268-270 (1985).
Seitz et al., "Tablet coating," in The theory and practice of industrial pharmacy, Lachman et al. eds., Lea and Febiger, pp. 346-373 (1986).
Selway et al., "Potential hazards of long-term acid suppression," Scand. J. Gastroenterol., 25, Supp. 178, pp. 85-92 (1990).

(56) References Cited

OTHER PUBLICATIONS

Hawkey et al., "Prophylaxis of aspirin-induced gasf ric mucosal bleeding with ranitidine," Aliment. Pharmacol. Therap., 2, pp. 245-252 (1988).
Hawkey et al., Scandinavian J. Gastroenterology, pp. 124-127 (1996) Handbook of Pharmaceutical Excipients, 5th Edition (2006).
Hawkey et al., Scandinavian J. Gastroenterology, pp. 170-173 (1986).
Hawkins & Hanks, J. Pain and Symptom Management, pp. 140-151 (2000).
Helander et al., "Structure and function of rat parietal cells during treatment with omeprazole, SCH 28080, SCH 32651, or ranitidine," Scan. J. Gastroenterol., 25, pp. 799-809 (1990).
Histamine H2 antagonist information on drugs.com website, downloaded Feb. 20, 2012.
Hogan et al., "Prescription of nonsteroidal anti-inflammatory drugs for elderly people in Alberta," Can. Med. Assoc., 151(3), pp. 315-322 (1994).
Howden, "Clinical Pharmacology of Omeprazole," Clin. Pharmacokinet, 20(1), pp. 38-49 (1991).
Ife et al., "Reversible inhibitors of the Gastric (H.sup.+/K.sup.+)-ATpase. 3. 3-Substituted-4-(phenylamino)quinolines," J. Med. Chem., 35, pp. 3413-3422 (1992).
Jiranek, et al., "Misoprostol Reduces Gastroduodenal Injury From One Week of Aspirin: An Endoscopic Study," Gastroenterology, 96, pp. 656-661 (1989).
Katz et al., "Gastric acidity and acid breakthrough with twice-daily omeprazole or iansoprazole," Aliment. Pharmacol. Ther., 14, pp. 709-714 (2000).
Keeling et al., "SK&F 96067 is a reversible, lumenally acting inhibitor of the gastric (H.sup.+ +K.sup.+)-ATPase," Biochemical Pharmacology, 42(1), pp. 123-130 (1991).
Kephart et al., "Coprescribing of nonsteroidal anti-inflammatory drugs and cytoprotective and antiulcer drugs in Nova Scotia's senior population," Clin. Ther., 17, pp. 1159-1173 (1995).
Kimmey et al., "Role of H2-receptor blockers in the prevention of gastric injury resulting from nonsteroidal anti-inflammatory agents," Am. J. Med., 84, pp. 49-52 (1988).
Kitchingman, et al., "Enhanced Gastric Mucosal Bleeding with Doses of Asprin Used for Prophylaxis and Its Reduction by Ranitidine," Br. J. Clin. Pharmac., 28, pp. 581-585 (1989).
Konturek et al., "Effects of omeprazole, a substituted benzimidazole, on gastrointestinal secretions, serum gastrin, and gastric mucosal blood flow in dogs," Gastroenterology, 86(1), pp. 71-77 (1984).
Lad et al., "Management of nonsteroidal anti-inflammatory drug-induced gastroduodenal disease by acid suppression," Can J. Gastroenterol., 13, pp. 135-142 (1999).
Lanas, A. "Prevention of aspirin-induced gastroduodenal damage: *H. pylori* infection eradication versus proton pump inhibitors or both," Digestive and Liver Disease, 36, pp. 655-657 (2004).
Lanza, et al., "A Double-Blind Placebo-Controlled Comparison of the efficacy and Safety of 50, 100, and 200 ug of Misoprostol QID in the Prevention of Ibuprofen-Induced Gastric and Duodenal Mucosal Lesions and Symptoms," Am. J Gastroenterol., 84(6), pp. 633-636 (1989).
Lanza, et al., "Double-Blind, Placebo-Controlled Endoscopic Comparison of the Mucosal Protective Effects of Misoprostol Versus Cimetidine on Tolmetin-Induced Mucosal Injury to the Stomach and Duodenum," Gastroenterology, 95, pp. 289-294 (1988).
Larsson et al., "Animal pharmadynamics of omeprazole. A survey of its pharmacological properties in vivo," Scand J Gastroenterol Suppl., 108, pp. 23-35 (1985).
Lee et al., "Omeprazole prevents indomethacin-induced gastric ulcers in rabbits," Aliment. Pharmacol. Ther., 10, pp. 571-576 (1996).
Leese, et al., "Effects of Celecoxib, a Novel Cyclooxygenase-2 Inhibitor, on Platelet Function in Healthy Adults: A Randomized, Controlled Trial," J. Clin. Pharmacol., 40, pp. 124-132 (2000).
Leonards et al., "Reduction or prevention of aspirin-induced occult gastrointestinal blood loss in man," Clinical Pharmacology and Therapeutics, 10(4), pp. 571-575 (1969).

Lichtenbergetr et al., "Nonsteroidal anti-inflammatory drug and phospholipid prodrugs: combination therapy with antisecretory agents in rats," Gastroenterology, 111, pp. 990-995 (1996).
Lin and Lu, "Role of pharmacokinetics and metabolism in drug discovery and development," Pharmacological Reviews, 49(4), pp. 403-449 (1997).
Maggi et al., Int. J. Pharm., pp. 173-179 (1993).
Mason et al., "Kinetics of aspirin, salicyclic acid, and salicyuric acid following oral administration of aspirin as a tablet and two buffered solutions," J. Pharmaceutical Sciences, 70(3), pp. 262-265 (1981).
Mattson et al., "Omeprazole provides protection against experimentally induced gastric mucosal lesions," Eur. J. Pharmacol., 91, pp. 111-114 (1983).
McKeage et al., "Esomeprazole: a review of its use in the management of gastric acid-related diseases in adults," Drugs, 68(11), pp. 1571-1607 (2008).
Miner et al., "Clinical trial: evaluation of gastric acid suppression with three doses of immediate-release esomeprazole in the fixed dose combination of PN400 (naproxen/esomeprazole magnesium) compared with naproxen 500 mg and enteric coated esomeprazole 20 mg: a randomized, open-label, phase 1 study in healthy volunteers," Alimentary pharmacology and therapeutics, 32, pp. 414-424, table 1 (2010).
Miner et al., "T1969 gastric acid suppression with PN400, a single-tablet, multilayer, fixed-dose formulation combining an immediate-release esomeprazole layer and an enteric-coated naproxen core," Gastroenterology, Elsevier, Philadelphia, PA, 136(5), p. A-611 (May 1, 2009).
Miner et al., "T1972 Pharmacokinetics of Naproxen and Esomeprazole in PN400, a single-tablet, multilayer formulation of enteric-coated Naproxen coupled with immediate-release Esomeprazole," Gastroenterology, Elsevier, Philadelphia, PA, 136(5), p. A-612 (May 1, 2009).
Morgner et al., "Esomeprazole: prevention and treatment of NSAID-induced symptoms and ulcers," Expert opinion on pharmacotherapeutics, 8(7), pp. 975-988 (2007).
Morris, et al., "Gastric Cyloprotection Is Secondary to Increased Mucosal Fluid Secretion: A Study of Six Cytoprotective Agents in the Rat," J. Clin. Gastroenterol., 27, Supp. 1, pp. S53-S63 (1998).
Morrison et al., "The optimal analgesic dose of rofecoxib: overview of six randomized controlled trials," JADA, 131, pp. 1729-1737 (2000).
Muller English translation—Muller, et al., "Untersuchungen zur Schutzwirkung von Lansoprazol auf die menschliche Magenschleimhaut gegenuber niedrig dosierter Acetylsalicylsaure," Arzneimittel Forschung, 47, pp. 758-760 (1997).
Muller English translation—Muller, et al., "Verbesserung der gastroduodenalen Vertraglichkeit von Azetylsalizylsaure durch Ranitidin," Arzneimittel-Forschung/Drug Res., 41(1), pp. 638-639 (1991).
Muller, et al., "Untersuchungen zur Schutzwirkung von Lansoprazol auf die menschliche Magenschleimhaut gegenuber niedrig dosierter Acetylsalicylsaure," Arzneimittel Forschung, 47, pp. 758-760 (1997).
Muller, et al., "Verbesserung der gastroduodenalen Vertraglichkeit von Azetylsalizylsaure durch Ranitidin," Arzneimittel-Forschung/Drug Res., 41(1), pp. 638-639 (1991).
Naesdal, et al., Gastro-Duodenal Protection in an Era of Cyclo-Oxygenase-2-Selective Nonsteroidal Anti-Inflammatory Drugs, European Journal of Gastroenterology & Hepatology, 13(12), pp. 1401-1406 (2001).
Naprosyn EC Label, Roche (1999).
Nefesoglu, et al., "Interaction of Omeprazole with Enteric-Coated Salicylate Tablets," International Journal of Clinical Pharmacology and Therapeutics, 36(10), pp. 549-553 (1998).
Neuvonen et al., "Enhancement of drug absorption of antacids," Clin. Pharmacokinet., 27(2), pp. 120-128 (1994).
Oddsson et al., "Endoscopic findings in the stomach and duodenum after treatment with enteric-coated and plain naproxen tablets in healthy subjects," Scand. J. Gastroenterol., 25, pp. 231-234 (1990).
Oddsson, et al., "Comparison between Ranitidine and Omeprazole for Protection against Gastroduodenal Damage Caused by Naproxen," Scand. J. Gastroenterol., 27, pp. 1045-1048 (1992).

(56) References Cited

OTHER PUBLICATIONS

Okabe et al., "Antisecretory effect of leminoprazole on histamine-stimulated gastric acid secretion in dogs: potent local effect," Jpn. J. Pharmacol., 69, pp. 91-100 (1995).

Okabe et al., "Pharmacological regulation of gastric acid secretion in the apical membrane of parietal cells; a new target for antisecretory drugs," Journal of Physiology and Pharmacology, 52(4), pp. 639-656 (2001).

Office Communication issued in Egyptian Patent Application No. 2121/2011, dated Apr. 13, 2013. (English summary of Arabic text).

"*Astrazeneca AB, Astrazeneca LP, KBI-E Inc., and Pozen, Inc.* v *Dr. Reddy's Laboratories Inc. and Dr. Reddy's Laboratories Ltd.*: Dr. Reddy's Laboratories Inc. and Dr. Reddy's Laboratories Ltd's. Invalidity contentions pursuant to L. Pat. R. 3.6(c)," dated Nov. 23, 2011.

"*Astrazeneca AB, Astrazeneca LP, KBI-E Inc., and Pozen, Inc.* V *Lupin Ltd. and Lupin Pharmaceuticals, Inc.*: Defendants Lupin Ltd. and Lupin Pharmaceuticals, Inc's Amended Invalidity Contentions Pursuant to L. Pat. R. 3.3 and 3.6(c)," dated Apr. 20, 2012.

"*Astrazeneca AB, Astrazeneca LP, KBI-E Inc., and Pozen, Inc.* v *Lupin Ltd. and Lupin Pharmaceuticals Inc.*: Defendants Lupin Ltd. and Lupin Pharmaceuticals, Inc.'s Invalidity Contentions Pursuant to L. Pat. R. 3.3 and 3.6(c)," dated Nov. 23, 2011.

"*Astrazeneca AB, Astrazeneca LP, KBI-E Inc., and Pozen, Inc.* v. *Anchen Pharmaceuticals, Inc.*: Anchen's Initial Invalidity Contentions," dated May 11, 2012.

"*Astrazeneca AB, Astrazeneca LP, KBI-E Inc., and Pozen, Inc.* v. *Dr. Reddy's Laboratories Inc. and Dr. Reddy's Laboratoriese Ltd.*: Plaintiffs' Response to DRL's First Set of Interrogatories to Plaintiffs (Nos. 1-5)," dated Mar. 5, 2012.

Notice of Paragraph IV Certification Re: Dr. Reddy's Laboratories, Ltd.'s and Dr. Reddy's Laboratories, Inc.'s Naproxen and Esomeprazole Magnesium Delayed Release Tablets; U.S. Patent No. 6,926,907, from Dr. Reddy's Laboratories, Ltd./Dr. Reddy's Laboratories, Inc., dated Mar. 11, 2011.

European Search Report issued in European Patent Application No. 09178773, dated Feb. 11, 2010.

Jacques et al., "Final purification, enrichment, of partially resolved enantiomer mixtures," In: *Enantiomers, Racemates, and Resolutions*, 423-434, 1981.

Letter to European Patent Office for European Application No. 02 734 602.2, regarding Oral Proceedings dated Dec. 18, 2009.

Notice of Opposition to a European Patent, submitted against European Patent Publication No. EP 1 411 900 on Apr. 15, 2011.

Notice of Opposition to a European Patent, submitted against European Patent Publication No. EP 1 411 900 on Apr. 20, 2011.

Office Communication issued in European Patent Application 10177150.9, dated Nov. 12, 2010.

Office Communication issued in European Patent Application No. 02734602.2, dated Feb. 22, 2010.

Office Communication issued in European Patent Application No. 02734602.2, dated Apr. 29, 2010.

Office Communication issued in European Patent Application No. 0273602.2, dated Jun. 21, 2010.

PCT International Preliminary Report on Patentability issued in International Application No. PCT/US2009/003281 dated Dec. 9, 2010.

PCT International Search Report and Written Opinion issued in International Application No. PCT/US2010/039864, dated Aug. 30, 2010.

PCT International Search Report issued in International Application No. PCT/US2002/17105, dated Mar. 14, 2003.

Ramage et al., "Inhibition of food stimulated acid secretion by misoprostol, an orally active synthetic E1 analogue prostaglandin," *Br. J. Clin Pharmac.*, 19:9-12, 1985.

*Remington's Pharmaceutical Sciences*, 17th ed., University of Sciences in Philadelphia, 1985.

Response to Office Communication filed in European Patent Application No. 02734602.2, dated May 10, 2010.

Takeuchi et al., "Effects of topical application of acidified omeprazole on acid secretion and transmucosal potential difference in anesthetized rat stomachs," *Japan J. Pharmacol.*, 47:397-1988.

Wilson et al., "Effects of misoprostol on gastric acid and mucus secretion in man," *Digestive Diseases and Sciences*, 31(2): 126S-129S, 1986.

Bajbouj et al., "A prospective multicenter clinical and endoscopic follow-up study of patients with gastroesophageal reflux disease." *Z. Gastroenterol.*, 43:1303-1307, 2005.

Chen et al., "Esomeprazole tablet vs. omeprazole capsule in treating erosive esophagitis," *World Journal of Gastroenterology*, 11(20):3112-3117, 2005.

Fass, "Erosive Esophagitis and Nonerosive Reflux Disease (NERD): Comparison of Epidemiologic, Physiologic, and Therapeutic Characteristics," *J. Clin. Gastroenterol.*, 41(2):131-137, 2007.

Goldstein et al., "PA32540 (Enteric-coated aspirin 325 mg + immediate-release omeprazole 40mg) is associated with sianificantly fewer gastric ulcers and significantly less endoscopic erosive esophagitis than enteric-coated aspirin (EC-ASA) alone: Results of two phase 3 studies," *The American Journal of Gastroenterology*, vol. 107, Suppl. 1, pp. S53-S54, 2012.

Johnson et al., "Esomeprazole once daily for 6 months is effective therapy for maintaining healed erosive esophagitis and for controlling gastroesophageal reflux disease symptoms: A randomized, double-blind, placebo-controlled study of efficacy and safety," *The American Journal of Gastroenterology*, 96(1):27-34, 2001.

Labenz et al., "Risk factors for erosive esophagitis: A multivariate analysis based on the proGERD study initiative," *American Journal of Gastroenterology*, 99:1652-1656, 2004.

Miner et al., "PA32540, a tablet containing enteric-coated (EC) aspirin 325 mg and unbuffered immediate-release omeprazole 40 mg, provides percent time gastric pH>4 significantly less than EC omeprazole 40 mg, but with faster onset and less exposure to omeprazole," *Gastroenterology*, vol. 142, Issue 5, Supplement 1. p. S-3, 2012.

Taha et al., "Famotidine for the prevention of peptic ulcers and oesophagitis in patients taking low-dose aspirin (FAMOUS): a phase III, randomized, double-blind, placebo-controlled trial," *Lancet*, 374:119-25, 2009.

Yeomans et al., "Efficacy of esomeprazole (20 mg once daily) for reducing the risk of gastroduodenal ulcers associated with continuous use of low-dose aspirin," *American Journal of Gastroenterology*, 103:1-9, 2008.

U.S. Department of Health and Human Services, Food and Drug Administration, Center for Drug Evaluation and Research, "Guidance for Industry SUPAC-MR: Modified Release Solid Oral Dosage Forms Scale-Up and Postapproval Changes: Chemistry, Manufacturing, and Controls; In Vitro Dissolution Testing and In Vivo Bioequivalence Documentation," available online at http://www.fda.gov/downloads/Drugs/Guidances/UCM070640.pdf, Sep. 1997.

World Health Organization, "Revision of Monograph on Tablets. Final text for addition to *The International Pharmacopoeia*," available online at http://www.who.int/medicines/publications/pharmacopoeia/Tabs-GeneralMono-rev-FINAL_31032011.pdf, Mar. 2011.

Sharma et al., "Comparison of 24-hour intragastric pH using four liquid formulations of lansoprazole and omeprazole," Am. J. Health-Syst. Pharm., 56, Supp. 4, pp. S18-S21 (1999).

Silverman, The Organic Chemistry of Drug Design and Drug Action, 2nd Edition, Academic Press, pp. 102 & 527 (2004).

Silverstein et al., "Gastrointestinal toxicity with celecoxib vs. nonsteroidal anti-inflammatory drugs for osteoarthritis and rheumatoid arthritis; the CLASS study: A randomized controlled trial," JAMA, 284, pp. 1247-1255 (2000).

Silverstein, et al., "Misoprostol Reduces Serious Gastrointestinal Complications in Patients with Rheumatoid Arthritis Receiving Nonsteroidal Anti-Inflammatory Drugs," Ann. Intern. Med., 123(4), pp. 241-249 (1995).

Simon English translation—Simon, et al., "Schutzwirkung von Omeprazol gegenuber niedrig dosierter Acetylsalicylsaure," Arzneimittel Forschung, 45, pp. 701-703 (1995).

(56) References Cited

OTHER PUBLICATIONS

Simon, et al., "Schutzwirkung von Omeprazol gegenuber niedrig dosierter Acetylsalicylsaure," Arzneimittel Forschung, 45, pp. 701-703 (1995).

Sung, "Management of nonsteroidal anti-inflammatory drug-related peptic ulcer bleeding," Am. J. Med., 110(1A), pp. 29S-32S (2001).

Tronstad et al., "Gastroscopic findings after treatment with enteric-coated and plain naproxen tablets in healthy subjects," Scand. J. Gastroenterol., 20, pp. 239-242 (1985).

Vane, et al., "The future of NSAID therapy: selective COX-2 inhibitors," IJCP, 54(1), pp. 7-9 (Jan./Feb. 2000).

Vimovo Press Release (Oct. 16, 2009).

von Unge et al., "Stereochemical assignment of the enantiomers of omeprazole from X-ray anaylysis of a fenchyloxymethyl derivative of (+)-(R)-omeprazole," Tetrahedron, 8(12), pp. 1967-1970 (1997).

Wagner et al., "Effects of nonsteroidal anti-inflammatory drugs on ulcerogenesis and gastric secretion in pylorus-ligated ligated rat," Digestive Diseases and Sciences, vol. 40, pp. 134-140 (1995).

Wakitani et al., "Profile of JTE-522 as a human cyclooxygenase-2 inhibitor," Jpn. J. Pharmacol., 78, pp. 365-371 (1998).

Wallmark et al., "The relationship between gastric acid secretion and gastric $H^+, K^+$-ATPase activity," J. Biol. Chem., 260(25), pp. 13681-13684 (1985).

Warner, et al., "Nonsteroid drug selectivities for cyclo-oxygenase-1 rather than cyclo-oxygenase-2 are associated with human gastrointestinal toxicity: A full in vitro analysis," Proc. Natl. Acad. Sci. USA, 96, pp. 7563-7568 (Jun. 1999).

Weil et al., "Prophylactic aspirin and risk of peptic ulcer bleeding," Br. Med. J., 310, pp. 827-830 (1995).

Wolfe et al., "Gastrointestinal toxicity of nonsteroidal anti-inflammatory drugs," N. Engl. J. Med., 340, pp. 1888-1899 (1999).

Wolfe, et al., "Acid Suppression: Optimizing Therapy for Gastroduodenal Ulcer Healing, Gastroesophageal Reflux Disease, and Stress Related Erosive Syndrome," Gastroenterology, 118(2), pp. S9-S31 (2000).

Yeomans et al., "A comparison of omeprazole with ranitidine for ulcers associated with nonsteroidal anti-inflammatory drugs," N. Engl. J. Med., 338, pp. 719-726 (1998).

Yeomans et al., "New data on healing of nonsteroidal anti-inflammatory drug-associated ulcers and erosions," Am. J. Med., 104, pp. 56S-61S (1998).

METHOD FOR TREATING A PATIENT AT RISK FOR DEVELOPING AN NSAID-ASSOCIATED ULCER

CROSS-REFERENCE TO RELATED APPLICATIONS

This application claims the benefit under 35 U.S.C. §119 (e) to U.S. Application Nos. 61/220,420 filed 25 Jun. 2009, 61/225,970 filed 16 Jul. 2009, and 61/310,525 filed 4 Mar. 2010, each of which is incorporated herein by reference.

The present disclosure is directed to a method for treating a disease or disorder in a patient at risk of developing an NSAID-associated ulcer by administering to said patient in need thereof a pharmaceutical composition in unit dose form comprising naproxen, or pharmaceutically acceptable salt thereof, and esomeprazole, or pharmaceutically acceptable salt thereof to said at risk patient and thereby decreasing the patient's risk of developing an ulcer.

Over 15 million Americans take NSAIDs each day to treat pain and/or inflammation. While NSAIDs remain a key therapy for pain and inflammation, there is a substantial risk of upper gastrointestinal (UGI) ulcerations and ulcer complications, such as, for example, bleedings and perforations, with chronic NSAID therapy. The cumulative incidence of gastroduodenal ulcers (GDUs) with conventional NSAID use has been reported to be as high as 25-30% at 3 months and 45% at 6 months versus 3-7% for placebo. At any given time, the incidence of UGI ulcers in NSAID users has been estimated to be as high as 30%. The risk factors associated with an NSAID user developing UGI ulcers include: age≥50 years, history of UGI ulcer or bleeding, or concomitant aspirin use. The mechanism associated with the increased incidence of ulcers in chronic NSAID users may be complex but it is thought that gastric acid, combined with a reduction in protective mechanisms of the UGI mucosa, contribute to this pathology. UGI mucosal injury includes petechia, erosions and ulcers. In addition, once mucosal injury occurs, acid has the ability to impair normal hemostasis and healing. These factors, coupled with the known anti-platelet effect of some NSAIDs, may increase the risk for gastrointestinal (GI) injury and bleeding. UGI effects of NSAIDs also include: dyspepsia (experienced by up to 40% of patients on NSAID therapy), erosive esophagitis (EE) (experienced by 21% of regular NSAID users), and an increase in gastroesophageal reflux disease symptoms. Additionally, the concurrent use of aspirin and an NSAID increases the risk of serious GI events.

A pharmaceutical formulation comprising immediate release (IR) esomeprazole magnesium and enteric-coated (EC) naproxen has been found to reduce the incidence of ulcers in patients at risk for developing NSAID-associated ulcers when compared to EC-naproxen. Such a formulation has also been found to reduce the incidence of ulcers in patients taking low dose aspirin (LDA) who are at risk for developing NSAID-associated ulcers when compared to EC-naproxen. Furthermore, patients taking this new formulation of IR esomeprazole and EC-naproxen were able to continue treatment longer than patients taking EC-naproxen.

In one aspect, the disclosure is directed to a method comprising: treating a disease or disorder in a patient at risk of developing an NSAID-associated ulcer by administering to said patient in need thereof a pharmaceutical composition in unit dose form comprising (a) esomeprazole, or pharmaceutically acceptable salt thereof, in an amount sufficient to raise the gastric pH of said patient to at least 3.5 upon administration of one or more of said unit dose forms, and (b) a therapeutically effective amount of naproxen, or pharmaceutically acceptable salt thereof; wherein said unit dose form provides for coordinated release of the esomeprazole and the naproxen such that: (i) at least a portion of said esomeprazole, or pharmaceutically acceptable salt thereof, is released independent of the pH of the surrounding medium; and (ii) the naproxen, or pharmaceutically acceptable salt thereof, is not released from said unit dose form until the pH of the surrounding medium is 3.5 or higher; and wherein said pharmaceutical composition in unit dose form decreases the risk of said patient developing an ulcer.

In another aspect, the disclosure is directed to a method of treating a disease or disorder in a patient at risk of developing an NSAID-associated ulcer by administering to the patient a pharmaceutical composition in unit dosage form suitable for oral administration comprising: (a) esomeprazole or pharmaceutically acceptable salt thereof, that is immediately soluble when the dosage form is placed in an aqueous medium, independent of pH, in an amount effective to raise the gastric pH of the patient to at least 3.5 upon administration of one or more of the unit dosage forms, and (b) naproxen or pharmaceutically acceptable salt thereof, wherein the naproxen or pharmaceutically acceptable salt thereof is surrounded by a coating that is substantially insoluble in an aqueous medium at a pH below 3.5 and at a temperature of about 37° C.; and wherein said pharmaceutical composition in unit dose form decreases the risk of said patient developing an ulcer.

In yet another aspect, the risk of NSAID-associated gastrointestinal ulcer in a patient may be associated with chronic NSAID treatment, age of the patient (for example if the patient is 50 years of age or older), the administration of aspirin prior to or during NSAID treatment (short-term or chronic treatment), or any combination thereof.

In still another aspect, the pharmaceutical composition in unit dose form disclosed herein decreases the risk of said patient developing a gastric ulcer, duodenal ulcer (DU), gastroduodenal ulcer, or combinations thereof.

In yet another aspect, the disease or disorder may be, for example, pain, inflammation, osteoarthritis, rheumatoid arthritis, ankylosing spondylitis, or any combination thereof.

In another aspect, the pharmaceutical composition in unit dose form disclosed herein is administered to said patient every day, for example twice a day. In further aspects, the pharmaceutical composition in unit dose form disclosed herein is administered to said patient for at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 18 months, or at least about 24 months, for example twice a day.

In a further aspect, the pharmaceutical compositions in unit dosage form disclosed herein may comprise esomeprazole or pharmaceutically acceptable salt thereof in an amount effective to raise the pH of the gastric fluid of a patient to at least 3.5, at least 4.0, at least 4.5, at least 5.0, or at least 5.5 when the dosage form is administered orally to said patient. The esomeprazole or pharmaceutically acceptable salt thereof may be present in the unit dosage form in an amount of from about 10 mg to about 50 mg, or in an amount of about 20 mg. In other embodiments, the pharmaceutical compositions in unit dosage form disclosed herein may comprise naproxen, or pharmaceutically acceptable salt thereof, in an amount of, for example, from about 200 mg to about 600 mg, about 375 mg, or about 500 mg.

In a still further aspect, the pharmaceutical composition is formulated for administration to a patient once daily or twice daily. In certain embodiments, the unit dosage form may be a tablet, a sequential-delivery tablet formulation, a capsule, a capsule containing beads, or minitablets. In one aspect, the unit dosage form is a tablet comprising a core and two or more layers, in which (i) the naproxen or pharmaceutically acceptable salt thereof is in the core; (ii) a first layer surrounds the core and said layer is a coating that is substantially insoluble in aqueous medium at a pH below 3.5 and/or at a temperature of about 37° C.; and (iii) at least one second layer that surround the first layer and comprises esomeprazole or pharmaceutically acceptable salt thereof. In some embodiments, the first layer may be, for example, an enteric coating or a time-release coating. In other embodiments, the unit dosage form may be surrounded by a pharmacologically inert, water soluble coating or film.

In yet still a further aspect, administering a unit dosage form disclosed herein to a patient in need thereof reduces the risk said patient will develop an ulcer more than if said patient were administered an enteric coated naproxen, or pharmaceutically acceptable salt thereof. In another embodiment, the administration of the unit dosage form disclosed herein improves compliance in a patient who requires short-term or chronic daily dosages of an NSAID, such as, for example, naproxen or pharmaceutically acceptable salt thereof.

In another aspect, the unit dosage form is a multilayer tablet comprising a core and at least a first layer enclosing the core, and a second layer enclosing the first layer, wherein: (i) the core comprises naproxen, or pharmaceutically acceptable salt thereof; (ii) the first layer is a coating that releases less than 10% of the naproxen after 2 hours when tested using the USP Paddle Method in 1000 ml of 0.1N HCl at 75 rpm at 37° C.+−0.5° C.; and (iii) the second layer comprises esomeprazole, or pharmaceutically acceptable salt thereof and at least one excipient, wherein the second layer is at least 95% soluble after 30 minutes when tested using the USP Paddle Method in 1000 ml of 0.1N HCl for two hours at 75 rpm at 37° C.+−0.5° C. The unit dosage form may further have a pharmacologically inert, water soluble coating or film surrounding the outermost layer of the unit dosage form, for example wherein the inert coating or film comprises a water soluble sugar.

In a further aspect, administering a unit dosage form disclosed herein to a patient in need thereof reduces said patient's heartburn associated symptoms more than treating said patient in need thereof with enteric coated naproxen, or pharmaceutically acceptable salt thereof.

Yet a further aspect is directed to a method of treating a disease or disorder in a patient at risk of developing an NSAID-associated ulcer by administering to the patient a pharmaceutical composition in unit dosage form suitable for oral administration comprising: (a) esomeprazole or pharmaceutically acceptable salt thereof, that is immediately soluble when the dosage form is placed in an aqueous medium, independent of pH, in an amount effective to raise the gastric pH of the patient to at least 3.5, at least 4.0, at least 4.5, at least 5.0, or at least 5.5 upon administration of one or more of the unit dosage forms, and (b) naproxen or pharmaceutically acceptable salt thereof, wherein the naproxen or pharmaceutically acceptable salt thereof is surrounded by a coating that is substantially insoluble in an aqueous medium at a pH below 3.5 and at a temperature of about 37° C.; wherein the pharmaceutical composition reduces said patient's dyspepsia associated symptoms. In certain embodiments, administering a unit dosage form disclosed herein to a patient in need thereof reduces said patient's dyspepsia associated symptoms more than treating said patient with enteric coated naproxen, or pharmaceutically acceptable salt thereof.

Abbreviations and/or special terms that may be used herein are set forth in Table 1 and the text that follows.

The definitions set forth herein take precedence over definitions set forth in any patent, patent application, and/or patent application publication incorporated herein by reference.

TABLE 1

Abbreviations and Special Terms

| Abbreviation | Explanation |
|---|---|
| AE | adverse event |
| ALT | alanine aminotransferase |
| ANCOVA | analysis of covariance |
| AST | aspartate aminotransferase |
| bid | twice daily |
| BUN | Blood urea nitrogen |
| CI | confidence interval |
| CMH | Cochran-Mantel-Haenszel |
| COX-2 | cyclo-oxygenase-2 |
| ECG | electrocardiogram |
| eCRF | electronic case report form |
| GCP | Good Clinical Practice |
| GERD | Gastroesophageal reflux disease |
| GI | gastrointestinal |
| IRB | institutional review board |
| ITT | intent-to-treat |
| LSM | least squares mean |
| MedDRA | Medical Dictionary for Regulatory Activities |
| OTE-DP | Overall Treatment Evaluation - Dyspepsia |
| PDS | Phoenix Data Systems |
| PP | per-protocol |
| PRO | patient reported outcomes |
| AE | adverse event |
| ALT | alanine aminotransferase |
| SAE | serious adverse event |
| SD | standard deviation |
| SOC | system organ class |
| SODA | Severity of Dyspepsia Assessment |
| UGI | upper gastrointestinal |

The term "at risk patient" refers to patient(s) at risk for NSAID associated ulcer due to age≥50 years, history of UGI ulcer or bleeding, and/or concomitant aspirin use. In one embodiment, the at risk patient is a patient at risk for NSAID associated ulcer due to age greater than or equal to 50 years. In another embodiment, the at risk patient is a patient at risk for NSAID associated ulcer due to concomitant aspirin use. In yet another embodiment, the at risk patient is a patient at risk for NSAID associated ulcer due to history of UGI ulcer or bleeding.

The term "enantiomerically pure" refers to a compound containing at least about 75% of the named enantiomer out of the total amount of the two possible enantiomers contained therein. In a particular embodiment, "enantiomerically pure" refers to a compound containing at least about 90% of the named enantiomer out of the total amount of the two possible enantiomers contained therein. In a more particular embodiment, "enantiomerically pure" refers to a compound containing at least about 95% of the named enantiomer out the total amount of the two possible enantiomers contained therein. In still a more particular embodiment, "enantiomerically pure" refers to a compound containing at least about 96% of the named enantiomer out the total amount of the two possible enantiomers contained therein. In still a further embodiment, "enantiomerically pure" refers to a compound containing at least about 97% of the named enantiomer out the total amount of the two possible enantiomers contained therein. In yet still a further embodiment, "enantiomerically pure" refers to a compound containing at least about 98% of the named enantiomer out the total amount of the two possible enantiomers contained therein. In yet a still even further embodiment, "enantiomerically pure" refers to a compound containing at least about 99% of the named enantiomer out the total amount of the two possible enantiomers contained therein. In another embodiment, "enantiomerically pure" refers to a compound containing at least about 99.9% of the named enantiomer out the total amount of the two possible enantiomers contained therein.

The term "low dose aspirin" refers to dosages of aspirin that are ≤325 mg.

The term "pharmaceutically acceptable", as employed herein, indicates the subject matter being identified as "pharmaceutically acceptable" is suitable and physiologically acceptable for administration to a patient/subject. For example, the term "pharmaceutically acceptable salt(s)" denotes suitable and physiologically acceptable salt(s).

The phrase "naproxen, or pharmaceutically acceptable salt thereof refers to the free base of naproxen, pharmaceutically acceptable salt(s) of naproxen, and/or mixtures of the free base of naproxen and at least one pharmaceutically acceptable salt of naproxen.

The phrase "esomeprazole, or pharmaceutically acceptable salt thereof refers to the free base of esomeprazole, pharmaceutically acceptable salt(s) of esomeprazole, and/or mixtures of the free base of esomeprazole and at least one pharmaceutically acceptable salt of esomeprazole.

The term "unit dosage form" (or "unit dose form") as used herein refers to a single entity for drug administration. For example, a single tablet or capsule containing both esomeprazole and naproxen is a unit dosage form. Unit dosage forms of the present disclosure provide for sequential drug release in a way that elevates gastric pH and reduces the deleterious effects of naproxen on the gastroduodenal mucosa, e.g., the esomeprazole is released first and the release of naproxen is delayed until after the pH in the GI tract has risen to 3.5 or greater. A "unit dosage form" (or "unit dose form") may also be referred to as a "fixed dosage form" (or "fixed dose form") or fixed dosage combination (or "fixed dose combination") and are otherwise interchangeable.

With regard to the dosages of each of naproxen, or pharmaceutically acceptable salt thereof and/or esomeprazole, or pharmaceutically acceptable salt thereof the term "about" is intended to reflect variations from the specifically identified dosages that are acceptable within the art.

With regard to the pH values and/or ranges recited herein, the term "about" is intended to capture variations above and below the stated number that may achieve substantially the same results as the stated number.

With regard to the term numerical values used in conjunction with the phrase "substantially free", the term is intended to capture variations above and below the stated number that may achieve substantially the same results as the stated number.

The phrase "substantially free" means from about 95% to about 99.99% free. In one embodiment, substantially free means about 95% free. In another embodiment, the term substantially free means about 96% free. In still another embodiment, the term substantially free means about 97% free. In yet another embodiment, the term substantially free means about 98% free. In a further embodiment, the term substantially free means about 99% free. In still a further embodiment, the term substantially free means about 99.99% free.

In the present disclosure, each of the variously stated ranges is intended to be continuous so as to include each numerical parameter between the stated minimum and maximum value of each range. For Example, a range of about 1 to about 4 includes about 1, 1, about 2, 2, about 3, 3, about 4, and 4.

One embodiment is directed to a method comprising: treating a disease or disorder in a patient at risk of developing an NSAID-associated ulcer by administering to said patient in need thereof a pharmaceutical composition in unit dose form comprising (a) esomeprazole, or pharmaceutically acceptable salt thereof, in an amount sufficient to raise the gastric pH of said patient to at least 3.5 upon administration of one or more of said unit dose forms, and (b) a therapeutically effective amount of naproxen, or pharmaceutically acceptable salt thereof; wherein said unit dose form provides for coordinated release of the esomeprazole and the naproxen such that: (i) at least a portion of said esomeprazole, or pharmaceutically acceptable salt thereof, is released independent of the pH of the surrounding medium; and (ii) the naproxen, or pharmaceutically acceptable salt thereof, is not released from said unit dose form until the pH of the surrounding medium is 3.5 or higher; and wherein said pharmaceutical composition in unit dose form decreases the risk of said patient developing an ulcer. Such pharmaceutical compositions have been described in U.S. Pat. No. 6,926,907, which is incorporated herein by reference in its entirety.

Another embodiment is directed to a method comprising: treating a disease or disorder in a patient in need of chronic NSAID treatment and at risk of developing an NSAID-associated ulcer by administering to said patient in need thereof a pharmaceutical composition in unit dose form comprising (a) esomeprazole, or pharmaceutically acceptable salt thereof, in an amount sufficient to raise the gastric pH of said patient to at least 3.5 upon administration of one or more of said unit dose forms, and (b) a therapeutically effective amount of naproxen, or pharmaceutically acceptable salt thereof; wherein said unit dose form provides for coordinated release of the esomeprazole and the naproxen such that: (i) at least a portion of said esomeprazole, or pharmaceutically acceptable salt thereof, is released independent of the pH of the surrounding medium; and (ii) the naproxen, or pharmaceutically acceptable salt thereof, is not released from said unit dose form until the pH of the surrounding medium is 3.5 or higher; and wherein said pharmaceutical composition in unit dose form decreases the risk of said patient developing an ulcer.

Still another embodiment, is directed to a method comprising: treating signs and symptoms of osteoarthritis, rheumatoid arthritis and ankylosing spondylitis in a patient at risk of developing an NSAID-associated ulcer by administering to said patient in need thereof a pharmaceutical composition in unit dose form comprising (a) esomeprazole, or pharmaceutically acceptable salt thereof, in an amount sufficient to raise the gastric pH of said patient to at least 3.5 upon administration of one or more of said unit dose forms, and (b) a therapeutically effective amount of naproxen, or pharmaceutically acceptable salt thereof; wherein said unit dose form provides for coordinated release of the esomeprazole and the naproxen such that: (i) at least a portion of said esomeprazole, or pharmaceutically acceptable salt thereof, is released independent of the pH of the surrounding medium; and (ii) the naproxen, or pharmaceutically acceptable salt thereof, is not released from said unit dose form until the pH of the surrounding medium is 3.5 or higher; and wherein said pharmaceutical composition in unit dose form decreases the risk of said patient developing an ulcer.

Still yet another embodiment is directed to a method comprising: treating signs and symptoms of osteoarthritis, rheumatoid arthritis and ankylosing spondylitis in a patient in need of chronic NSAID treatment and at risk of developing an NSAID-associated ulcer by administering to said patient in need thereof a pharmaceutical composition in unit dose form comprising (a) esomeprazole, or pharmaceutically acceptable salt thereof, in an amount sufficient to raise the gastric pH of said patient to at least 3.5 upon administration of one or more of said unit dose forms, and (b) a therapeutically effective amount of naproxen, or pharmaceutically acceptable salt thereof; wherein said unit dose form provides for coordinated release of the esomeprazole and the naproxen such that: (i) at least a portion of said esomeprazole, or pharmaceutically acceptable salt thereof, is released independent of the pH of the surrounding medium; and (ii) the naproxen, or pharmaceutically acceptable salt thereof, is not released from said unit dose form until the pH of the surrounding medium is 3.5 or higher; and wherein said pharmaceutical composition in unit dose form decreases the risk of said patient developing an ulcer.

In a further embodiment, said disease or disorder treated by the pharmaceutical compositions disclosed herein is selected from pain and inflammation.

In yet another embodiment, said disease or disorder treated by the pharmaceutical compositions disclosed herein is selected from osteoarthritis, rheumatoid arthritis, ankylosing spondylitis, and a combination thereof.

In yet a further embodiment, said patient at risk of developing an NSAID associated ulcer is ≥50 years old.

In still yet another embodiment, said patient at risk of developing an NSAID associated ulcer has a history of UGI ulcer or bleeding.

In still even yet another embodiment, said patient is taking low dose aspirin.

In a still even further embodiment, said pharmaceutical composition in unit dose form decreases the risk of said patient developing a gastroduodenal ulcer.

In yet a further embodiment, said pharmaceutical composition in unit dose form decreases the risk of said patient developing a duodenal ulcer.

In a further embodiment, said pharmaceutical composition in unit dose form decreases the risk of said patient developing a gastric ulcer.

In yet another embodiment, administering said pharmaceutical composition in unit dose form to patients in need of NSAID treatment resulted in fewer patients developing a gastric ulcer than patients in need of NSAID treatment who were administered EC-naproxen.

In another embodiment, administering said pharmaceutical composition in unit dose form to patients in need of NSAID treatment resulted in from about 1% to about 12% of said patients developing a gastric ulcer.

In still another embodiment, administering EC-naproxen to patients in need of NSAID treatment resulted in from about 17% to about 31% of said patients developing a gastric ulcer.

In yet another embodiment, administering said pharmaceutical composition in unit dose form to patients in need of NSAID treatment resulted in fewer patients developing a duodenal ulcer than patients in need of NSAID treatment who were administered EC-naproxen.

In another embodiment, administering said pharmaceutical composition in unit dose form to patients in need of NSAID treatment resulted in from about 0% to about 2% of said patients developing a duodenal ulcer.

In still another embodiment, administering EC-naproxen to patients in need of NSAID treatment resulted in from about 3.5% to about 8% of said patients developing a duodenal ulcer.

In yet another embodiment, administering said pharmaceutical composition in unit dose form and low dose aspirin to patients in need of NSAID treatment resulted in fewer patients developing a gastric ulcer than patients administered EC-naproxen and low dose aspirin.

In another embodiment, administering said pharmaceutical composition in unit dose form and low dose aspirin to patients in need of NSAID treatment resulted in from about 0% to about 9% of said patients developing a gastric ulcer.

In still another embodiment, administering EC-naproxen and low dose aspirin to patients in need of NSAID treatment resulted in from about 20% to about 38% of said patients developing a gastric ulcer.

In yet another embodiment, administering said pharmaceutical composition in unit dose form and low dose aspirin to patients in need of NSAID treatment resulted in fewer patients developing a gastroduodenal ulcer than patients administered EC-naproxen and low dose aspirin.

In another embodiment, administering said pharmaceutical composition in unit dose form and low dose aspirin to patients in need of NSAID treatment resulted in from about 1.0% to about 10% of said patients developing a gastroduodenal ulcer.

In still another embodiment, administering EC-naproxen and low dose aspirin to patients in need of NSAID treatment resulted in from about 23% to about 42% of said patients developing a gastroduodenal ulcer.

In a yet still further embodiment, said patient was treated longer with said pharmaceutical composition in unit dose form than with EC-naproxen.

In yet another embodiment, patient compliance with long-term treatment is improved with the pharmaceutical compositions disclosed herein as compared to EC-naproxen.

In a yet even further embodiment, said pharmaceutical composition in unit dose form is a multilayer tablet comprising at least one core and at least a first layer and a second layer, wherein:

(i) said core comprises naproxen, or pharmaceutically acceptable salt thereof;

(ii) said first layer is a coating that at least begins to release the naproxen, or pharmaceutically acceptable salt thereof, when the pH of the surrounding medium is about 3.5 or greater; and (iii) said second layer is esomeprazole, or pharmaceutically acceptable salt thereof, wherein said esomeprazole, or pharmaceutically acceptable salt thereof, is released at a pH of from about 0 or greater.

In a further embodiment, said esomeprazole, or pharmaceutically acceptable salt thereof, is released from said multilayer tablet at a pH of from about 1 or greater.

In a yet further embodiment, said esomeprazole, or pharmaceutically acceptable salt thereof, is released from said multilayer tablet at a pH of from about 0 to about 2.

In yet still a further embodiment, esomeprazole, or pharmaceutically acceptable salt thereof, is released at a pH of from 0 to 2.

In a still further embodiment, at least a portion of said esomeprazole, or pharmaceutically acceptable salt thereof, contained in said multilayer tablet is not coated with an enteric coating.

In a yet still further embodiment, said first layer of said multilayer tablet is an enteric coating.

In a yet even still further embodiment, said multi-layer tablet is substantially free of sodium bicarbonate.

In another embodiment, the first layer is a coating that at least begins to release the naproxen, or pharmaceutically acceptable salt thereof, when the pH of the surrounding medium is about 4.0, 4.5, 5.0 or greater.

In a further embodiment, said first layer of said multi-layer tablet begins to release the naproxen, or pharmaceutically acceptable salt thereof, when the pH of the surrounding medium is at about 4.0 or greater.

In a yet still even further embodiment, said first layer of said multi-layer tablet begins to release the naproxen, or pharmaceutically acceptable salt thereof, when the pH of the surrounding medium is at about 4.5 or greater.

In yet a further embodiment, said first layer of said multi-layer tablet begins to release the naproxen, or pharmaceutically acceptable salt thereof, when the pH of the surrounding medium is at about 5.0 or greater.

In a still even further embodiment, the amount of esomeprazole, or pharmaceutically acceptable salt thereof, sufficient to raise the gastric pH is 20 mg.

In another embodiment, the esomeprazole is enantiomerically pure.

In still yet another embodiment, the therapeutically effective amount of naproxen, or pharmaceutically acceptable salt thereof, is selected from 375 mg and 500 mg.

In a still yet further embodiment, the therapeutically effective amount of naproxen, or pharmaceutically acceptable salt thereof, is 375 mg.

In an even still further embodiment, the therapeutically effective amount of naproxen, or pharmaceutically acceptable salt thereof, is 500 mg.

In another embodiment, naproxen can be present as the free base.

In yet another embodiment, naproxen can be present in equivalent amounts of pharmaceutically acceptable salts of naproxen, e.g., sodium naproxen.

In a further embodiment, esomeprazole can be present as a magnesium salt.

In a further embodiment, esomeprazole, or pharmaceutically acceptable salt thereof, can be present in an amount to provide about 15 mg of esomeprazole.

In still yet another embodiment, esomeprazole, or pharmaceutically acceptable salt thereof, can be present in an amount to provide about 30 mg of esomeprazole.

In one embodiment, the pharmaceutical composition in unit dose form comprises about 500 mg of said naproxen, or pharmaceutically acceptable salt thereof, and about 20 mg of said esomeprazole, or pharmaceutically acceptable salt thereof.

In another embodiment, the pharmaceutical composition in unit dose form comprises about 500 mg of said naproxen, or pharmaceutically acceptable salt thereof, and about 30 mg of said esomeprazole, or pharmaceutically acceptable salt thereof.

In yet another embodiment, the pharmaceutical composition in unit dose form comprises about 500 mg of said naproxen, or pharmaceutically acceptable salt thereof, and about 15 mg of said esomeprazole, or pharmaceutically acceptable salt thereof.

In still another embodiment, the pharmaceutical composition in unit dose form comprises about 375 mg of said naproxen, or pharmaceutically acceptable salt thereof, and about 15 mg of said esomeprazole, or pharmaceutically acceptable salt thereof.

In still yet another embodiment, the pharmaceutical composition in unit dose form comprises about 375 mg of said naproxen, or pharmaceutically acceptable salt thereof, and about 20 mg of said esomeprazole, or pharmaceutically acceptable salt thereof.

In a further embodiment, the pharmaceutical composition in unit dose form comprises about 375 mg of said naproxen, or pharmaceutically acceptable salt thereof, and about 30 mg of said esomeprazole, or pharmaceutically acceptable salt thereof.

In certain embodiments, the unit dosage form of the pharmaceutical compositions disclosed herein may comprise esomeprazole, or pharmaceutically acceptable salt thereof, naproxen, or pharmaceutically acceptable salt thereof, carnauba wax, colloidal silicon dioxide, croscarmellose sodium, iron oxide yellow, glyceryl monostearate, hypromellose, iron oxide black, magnesium stearate, methacrylic acid copolymer dispersion, methylparaben, polysorbate 80, polydextrose, polyethylene glycol, povidone, propylene glycol, propylparaben, titanium dioxide, and triethyl citrate.

In an even further embodiment, the pharmaceutical composition in unit dose form is a multilayer tablet comprising a core comprising naproxen, or pharmaceutically acceptable salt thereof, and a first layer comprising a coating that at least begins releasing the naproxen when the pH of the surrounding medium is about 3.5 or greater and a second layer comprising esomeprazole, or pharmaceutically acceptable salt thereof, wherein at least a portion of said esomeprazole, or pharmaceutically acceptable salt thereof, is not surrounded by an enteric coating.

In one embodiment, at least about 95% of the esomeprazole, or pharmaceutically acceptable salt thereof, is not surrounded by an enteric coating.

In another embodiment, at least about 99% of the esomeprazole, or pharmaceutically acceptable salt thereof, is not surrounded by an enteric coating. In yet another embodiment, at least about 99.5% of the esomeprazole, or pharmaceutically acceptable salt thereof, is not surrounded by an enteric coating.

In yet another embodiment, the multilayer tablet is substantially free of sodium bicarbonate.

In still another embodiment, the multilayer tablet is completely (i.e., 100%) free of sodium bicarbonate.

In one embodiment, the dosing regimen of the pharmaceutical compositions disclosed herein is twice a day.

In another embodiment, the doses can be separated by a period of at least about 10 hours.

In another embodiment, the pharmaceutical composition in unit dose form is given before a patient ingests a meal, for example about 30-60 minutes prior to ingesting a meal.

In another embodiment, the pharmaceutical compositions of the present disclosure may be administered therapeutically to patients either short term or over a longer period of time, for example chronically.

In yet another embodiment, fewer patients in need of NSAID treatment discontinued treatment with said pharmaceutical composition in unit dose form than discontinued EC-naproxen.

In still another embodiment, at least one upper gastrointestinal adverse event led from about 1% to about 9% of said patients in need of NSAID treatment to discontinue treatment with said pharmaceutical composition in unit dose form.

In yet still another embodiment, at least one upper gastrointestinal adverse event led from about 8% to about 17% of said patients in need of NSAID treatment to discontinue treatment with EC-naproxen.

In a still further embodiment, at least one upper gastrointestinal adverse event led from about 1% to about 9% of said patients in need of NSAID treatment to discontinue treatment with said pharmaceutical composition in unit dose form versus from about 8% to about 17% of said patients in need of NSAID treatment to discontinue treatment with EC-naproxen.

In yet another embodiment, a patient is ≥60 years of age and administration of the unit dose form to the patient results in an 70 to 100% relative risk reduction of the patient developing a gastric ulcer than a patient≥60 years of age who is treated with enteric coated naproxen, or pharmaceutically acceptable salt thereof.

In still yet another embodiment, a patient is ≥60 years of age and administration of the unit dose form to the patient results in an 89.2% relative risk reduction of the patient developing a gastric ulcer than a patient≥60 years of age who is treated with enteric coated naproxen, or pharmaceutically acceptable salt thereof.

In a further embodiment, a patient is 60-69 years of age and administration of the unit dose form to the patient results in an 86.4% relative risk reduction of the patient developing a gastric ulcer than a patient 60-69 years of age who is treated with enteric coated naproxen, or pharmaceutically acceptable salt thereof.

In an even further embodiment, a patient is ≥70 years of age and administration of the unit dose form to the patient results in a 100% relative risk reduction of the patient developing a gastric ulcer than a patient≥70 years of age who is treated with enteric coated naproxen, or pharmaceutically acceptable salt thereof.

The pharmaceutical compositions disclosed herein include, but are not limited to, for example, tablets and capsules that can be made in accordance with methods that are standard in the art (see, e.g., *Remington's Pharmaceutical Sciences*, $16^{th}$ ed., A Oslo editor, Easton, Pa. (1980)).

Suitable carriers include, but are not limited to: water; salt solutions; alcohols; gum arabic; vegetable oils; benzyl alcohols; polyethylene glycols; gelatin; carbohydrates such as lactose, amylose or starch; magnesium stearate; talc; silicic acid; paraffin; perfume oil; fatty acid esters; hydroxymethylcellulose; polyvinyl pyrrolidone; carnauba wax; colloidal silicon dioxide; croscarmellose sodium; glyceryl monostearate; hypromellose; methacrylic acid copolymer dispersion; methylparaben; polysorbate 80; polydextrose; povidone; propylene glycol; propylparaben; titanium dioxide; and triethyl citrate.

The pharmaceutical compositions disclosed herein can be sterilized and, if desired, mixed with, for example, auxiliary agents, such as, for example, preservatives; stabilizers; buffers; coloring agents; and flavoring agents.

In one embodiment, at least one of the layers comprising the pharmaceutical compositions disclosed herein may be applied using standard coating techniques. The layer materials may be dissolved or dispersed in organic or aqueous solvents. The layer materials may include, but are not limited to, for example, one or more of the following materials: methacrylic acid copolymers, shellac, hydroxypropylmethcellulose phthalate, polyvinyl acetate phthalate, hydroxypropylmethyl-cellulose trimellitate, carboxymethylethyl-cellulose, cellulose acetate phthalate, and/or other suitable polymer(s). The pH at which the first layer dissolves can be controlled by the polymer or combination of polymers selected and/or ratio of pendant groups. For example, dissolution characteristics of the polymer film can be altered by the ratio of free carboxyl groups to ester groups. The layers may also contain pharmaceutically acceptable plasticizers, such as, for example, triethyl citrate, dibutyl phthalate, triacetin, polyethylene glycols, polysorbates or other plasticizers. Additives, such as, for example, dispersants, colorants, anti-adhering, and anti-foaming agents may also be used.

In one embodiment, the pharmaceutical compositions disclosed herein can be in the form of a bi- or multi-layer tablet. In a bi-layer tablet, one portion/layer of the tablet contains the esomeprazole, or pharmaceutically acceptable salt thereof, in the required dose along with appropriate excipients, agents to aid dissolution, lubricants, fillers, etc.; and a second portion/layer of the tablet contains the NSAID in the required dose along with other excipients, dissolution agents, lubricants, fillers, etc.

In another embodiment, the naproxen portion/layer is surrounded by a polymeric coating that dissolves at a pH of at least about 3.5 or greater.

In yet another embodiment, the naproxen portion/layer is surrounded by a polymeric coating that dissolves at a pH of at least about 4 or greater.

The naproxen, or pharmaceutically acceptable salt thereof, may be granulated by methods such as slugging, low- or high-shear granulation, wet granulation, or fluidized-bed granulation. Of these processes, slugging generally produces tablets of less hardness and greater friability. Low-shear granulation, high-shear granulation, wet granulation and fluidized-bed granulation generally produce harder, less friable tablets.

EXAMPLE(S)

The invention is further defined in the following Example(s). It should be understood the Example(s) are given by way of illustration only. From the above discussion and the Example(s), one skilled in the art can ascertain the essential characteristics of the invention, and without departing from the spirit and scope thereof, can make various changes and modifications to adapt the invention to various uses and conditions. As a result, the invention is not limited by the illustrative example(s) set forth hereinbelow, but rather defined by the claims appended hereto.

Example 1

A 6-Month, Phase 3, Randomized, Double-Blind, Parallel-Group, Controlled, Multi-Center Study to Evaluate the Incidence of Gastric Ulcers (GUs) Following Administration of Either PN400, Which is a Single-Tablet Formulation Designed to Provide Sequential Delivery of Immediate-Release (IR) Esomeprazole (20 mg) and Enteric-Coated (EC) Naproxen (500 mg), or EC-Naproxen (500 mg) Alone in Subjects Who are at Risk for Developing NSAID-Associated Ulcers Methodology:

Two randomized, 6 month, Phase 3, double-blind, parallel group, controlled, multicenter studies (hereinafter known as Study A and Study B) enrolled *H. pylori*-negative male or non-pregnant, non-breastfeeding female subjects with osteoarthritis (OA), rheumatoid arthritis (RA), ankylosing spondylitis or other medical condition(s) expected to require daily NSAID therapy for at least 6 months, who were either (i) 18-49 years of age and had a history of a documented, uncomplicated gastric or duodenal ulcer (a mucosal break of at least 3 mm in diameter with depth, without any concurrent bleeding, clot or perforation) within the past 5 years, OR (ii) 50 years of age and older (these subjects did not require a history of a documented, uncomplicated gastric or duodenal ulcer within the past 5 years.).

Eligible subjects were randomized 1:1 to receive either PN400 (EC-naproxen 500 mg/immediate-release esomeprazole 20 mg) twice daily (bid) (one dose 30-60 minutes before breakfast or first meal of the day and the other dose 30-60 minutes before dinner) or EC-naproxen 500 mg bid (one dose 30-60 minutes before breakfast or first meal of the day and the other dose 30-60 minutes before dinner), stratified by low-dose aspirin (LDA) use (Yes/No) at randomization for 6 months or until gastroduodenal ulcer (GDU) was confirmed by endoscopy. The Primary endpoint was the incidence of gastric ulcer (GU) ($\geq 3$ mm diameter with depth) as determined by endoscopy at 1, 3 and 6 mos. A post-hoc pooled analysis of GU incidence in the 20-25% of patients using LDA was conducted. The incidence of endoscopic duodenal ulcer (DU), pre-specified NSAID-associated upper gastro intestinal adverse events (UGI AEs), and safety were secondary endpoints. This study consisted of a Screening Visit, a washout period for disallowed medications of 14 days, a second Screening/Baseline Endoscopy Visit and up to 4 outpatient visits over a 6-month period, or until GUs or DUs were confirmed by endoscopy. If a GU, DU or esophageal ulcer was detected, study drug was discontinued and the subject was discontinued from the study and placed on appropriate medication to treat the ulcer. A subject was considered to have completed the study if all scheduled assessments at the 6 month visit had been performed, or the primary efficacy endpoint (GU confirmed by endoscopy) had been reached prior to 6 months.

Clinical laboratory safety testing, measurement of vital signs, and endoscopy were performed at the Screening Visit and each Follow-up Visit. In addition, subjects had assessments for dyspepsia and related gastrointestinal (GI) symptoms using the Severity of Dyspepsia Assessment (SODA) instrument and heartburn symptoms at baseline (the day of randomization) and each post-baseline visit. Subjects who completed 6 months of therapy, discontinued due to GU, or discontinued prematurely returned for a Final Visit for endoscopy (excluding subjects with GU or DU), SODA and Overall Treatment for Dyspepsia (OTE-DP) questionnaires and heartburn assessments.

Number of Subjects (Planned and Analyzed):

Study A: 438 subjects were randomized, 434 subjects were treated, and 333 subjects completed the study. The data from 434 subjects was analyzed for efficacy.

Study B: 423 subjects were randomized, 420 subjects were treated, and 304 subjects completed the study. The data from 420 subjects was analyzed for efficacy.

Demographics ITT Population:

Study A:

Approximately 69% were female and 84% were white. The mean age was approximately 61 years, with about half of the subjects in both treatment groups being 50-59 years of age and $\geq 60$ years of age; a small percentage of the subjects (<3%) were <50 years of age. The majority (>85%) were non-smokers. There were no relevant differences in demographic characteristics between treatments. The 2 treatment groups were also similar with regard to baseline characteristics of ulcer history and NSAID use. Approximately 7% of the PN400 treatment group and 6% of the EC-naproxen group reported an ulcer within the last 5 years. Approximately 24% of PN400 subjects and 24% of EC-naproxen subjects were using LDA at randomization. OA was the most frequently reported reason for NSAID use. There were small differences in distribution of underlying etiologies between the two treatment groups. Most of the "other" indications for NSAID use were back pain, chronic back pain, low back pain (in 49 subjects). Of the LDA users, 89% in PN400 and 78% in EC-Naproxen treatment groups took an 81 mg dosage and 8% in PN400 and 20% in EC-Naproxen treatment groups took a 325 mg dosage.

Study B:

Approximately ⅔ were female and 89% were white. The mean age was approximately 60 years, with about half of the subjects in both treatment groups being 50-59 years of age and half being $\geq 60$ years of age; a small percentage of the subjects (approximately 3%) was <50 years of age. The majority (approximately 82%) were non-smokers. There were no relevant differences in demographic characteristics between treatments. The 2 treatment groups were similar with regard to most baseline characteristics. Approximately 22% of PN400 subjects and 24% of EC-naproxen subjects were using LDA at randomization. Approximately 9% of the PN400 treatment group and 11% of the EC-naproxen group reported an ulcer within the last 5 years. OA was the most frequently reported reason for NSAID use. There were small differences in distribution of underlying etiologies between the two treatment groups. Most of the "other" indications for NSAID use were back pain, chronic back pain, or low back pain (in 42 subjects). Of the LDA users, 80% in PN400 and 77% in EC-Naproxen treatment groups took an 81 mg dosage and 17% in PN400 and 20% in EC-Naproxen treatment groups took a 325 mg dosage.

Diagnosis and Main Criteria for Inclusion:

Subjects were males or non-pregnant, non-breastfeeding females at least 18 years of age with a medical condition expected to require daily NSAID therapy for at least 6 months, and, if less than 50 years old, with a documented history of GU or DU within the past 5 years. Eligible subjects were *Helicobacter pylori*-negative and did not have a GU or DU at Baseline.

Test Product, Dose, and Mode of Administration:

PN400 tablets were manufactured by Patheon Pharmaceuticals, Inc. (Cincinnati, Ohio) and contain EC-naproxen 500 mg and IR esomeprazole 20 mg (present as 22.3 mg esomeprazole magnesium trihydrate salt) given orally bid.

Reference Therapy, Dose, and Mode of Administration:

EC-naproxen 500 mg tablet (manufactured by Patheon Pharmaceuticals, Inc., Cincinnati, Ohio) given orally bid.

Visit Windows:

Visit windows used for determining the month of observed gastric or duodenal ulcer for efficacy analysis were as follows: (1) the 1 month visit included a planned visit day at 30±6 days (visit window based on actual study day was 1-36 days); (2) the 3 months visit included a planned visit day at 90±12 days (visit window based on actual study day was 37-108 days); and (3) the 6 months visit included a planned visit day at 180±12 days (visit window based on actual study day was ≥109 days). The study windows were used to determine the month of observation throughout the 6-month treatment period.

Objectives

Primary:

To demonstrate that PN400 is effective in reducing the risk of GUs in subjects at risk for developing NSAID-associated GUs.

Secondary:

(1) To determine if PN400 is effective in reducing the risk of DUs in subjects at risk for developing NSAID-associated ulcers.

(2) To compare UGI symptoms in subjects treated with PN400 versus EC-naproxen as measured by scores on SODA instrument and the OTE-DP.

(3) To compare heartburn symptoms in subjects treated with PN400 versus EC-naproxen.

(4) To evaluate the safety and tolerability of PN400 versus EC-naproxen.

Other:
To assess the effect of concomitant use of LDA (≤325 mg) on the incidence of GDUs within each treatment group.

Criteria for Evaluation:

Efficacy:
Efficacy was assessed by gastroduodenal endoscopy at Screening and at 1, 3 and 6 months visits and by Patient Reported Outcomes (PRO) questionnaires throughout the study.

Safety:
Safety was assessed by monitoring adverse events (AEs), serious AEs (SAES), clinical laboratory evaluations, vital signs, and physical examinations.

Statistical Methods:
All statistical analyses and data listings were completed using the SAS® system, version 9.1 or higher. Unless otherwise specified, all statistical tests were 2-sided, and statistical significance was tested at the 5% level.

Analysis Populations:
The following analysis populations were used:
  Intent-to-treat (ITT) population: All randomized subjects who received at least 1 dose of study drug and had no ulcer detected by endoscopy at the Screening Visit.
  Per-protocol (PP) population: All subjects in the ITT population who did not violate the protocol in any major way that would have impacted the evaluation of efficacy and had at least 70% overall treatment compliance. Subjects excluded from the PP population were identified prior to unblinding of the treatment code, and the reason for exclusion was documented.
  Safety population: All randomized subjects who received at least 1 dose of study drug.

Sample Size:
The sample size of 200 subjects per treatment group per Study A and Study B was based on the assumption that 15% of subjects treated with EC-naproxen would have a GU over the 6 months study duration compared to 5% of subjects treated with PN400. The computation used a Fisher's exact test, with a 2-sided significance level of 5% and 90% power to detect the difference between EC-naproxen and PN400.

Efficacy and Tolerability:
The primary efficacy endpoint was the proportion of subjects developing GUs throughout 6 months of study treatment. The observed cumulative incidence of GUs at 1, 3 and 6 months was summarized with its associated 95% confidence interval (CI) for each treatment group. Treatment groups were compared using a Cochran-Mantel-Haenszel (CMH) test stratified by use of LDA (Yes/No) at randomization.

In addition, the proportion of subjects developing GUs was estimated using the Kaplan-Meier method. Time to GU was calculated from the first day of study drug dispensed to the date of confirmed GU or was censored at the 6-month endoscopic assessment date or at the last assessment date if no GU developed. The Kaplan-Meier estimate and corresponding 95% CI for regrouped by-month data were calculated by treatment group at 1, 3, and 6 months. Kaplan-Meier time-to-event curves for the cumulative proportion of subjects developing GUs were plotted by treatment group. A log-rank test stratified by use of LDA (Yes/No) at randomization was used to test the difference between treatment groups in the survival curves.

The estimated and observed proportions of subjects developing GDUs throughout 6 months of treatment with LDA use (Yes/No) at randomization were summarized between treatment groups and within each treatment group in a similar fashion to the primary efficacy endpoint. To obtain an adequate power to assess the effect of LDA use between treatment groups, the statistical inference test was performed using the pooled data from Study A and Study B.

Concomitant medications were tabulated by therapeutic drug class and generic drug name using the World Health Organization Drug classification (March, 2007). The percentage of subjects who took acetaminophen and/or liquid antacid was tabulated for each treatment. The treatment difference in liquid antacid and acetaminophen use was analyzed using a Cochran-Mantel-Haenszel (CMH) test adjusting for use of LDA (Yes/No) at randomization. The total tablets/ounces taken per subject and average tablets/ounces taken per subject were summarized for each medication by treatment group.

The exposure to study drug was evaluated by days on study drug, total number of doses taken per subject and average doses taken per month for each subject and summarized using descriptive statistics. The duration of study drug exposure was also categorized as ≤1 month (days≤36), 1-3 months (36<days≤108), and 3-6 months (days>108) and tabulated by treatment group.

Treatment compliance for each visit per subject was defined as the percentage of total number of doses taken out of the scheduled number of doses between visits when the subject was in the study. Treatment compliance over the entire duration of study drug per subject was defined as the total number of doses taken out of the scheduled number of doses during the treatment period. Treatment compliance for each visit and overall was categorized as <50%, 50% to <70%, and ≥70% and summarized by treatment group. The overall treatment compliance was summarized using descriptive statistics.

Key Secondary Efficacy and Tolerability Endpoints were:
1. proportion of subjects with pre-specified NSAID-associated UGI AEs or DUs;
2. proportion of subjects discontinuing from the study due to NSAID-associated UGI AEs or DUs; and
3. proportion of subjects developing DUs throughout 6 months of study treatment.

Analyses of these endpoints were in sequential order, and the hierarchical fixed-sequence testing approach was used to adjust for multiple comparisons. These endpoints were tested in the specified sequence with the rule that once a p-value exceeded 0.05, endpoints further down in the sequence were not claimed for statistical significance. Treatment comparisons of the first 2 key secondary (tolerability) endpoints were performed using a CMH test adjusting for low-dose aspirin use (Yes/No) at randomization. Subjects who developed both GUs and DUs were not counted as discontinued due to DUss since subjects developing GUs were considered as completers. The proportion of subjects developing DUs throughout 6 months was analyzed in the same manner as the primary efficacy endpoint.

Non-Key Secondary Efficacy and Tolerability Endpoints Included:
  proportion of subjects with resolution of symptoms on the heartburn questionnaire;
  responses on the OTE-DP questionnaire;
  mean change from Baseline on each of the SODA subscales; and
  proportion of subjects discontinuing from the study due to any AE (including DU).

These were analyzed using a CMH test, modified Wilcoxon rank-sum (Van Elteren) test, ANCOVA, and a CMH test, respectively. In addition, the proportion of subjects developing GUs and/or DUs was analyzed in the same manner as the primary endpoint. All analyses were adjusted for use of LDA at randomization.

Safety:

All AEs were coded into preferred terms according to MedDRA (Medical Dictionary for Regulatory Activities) and classified by system organ class (SOC). Summaries of the incidence of all treatment-emergent AEs, treatment-related AEs, SAES, and AEs leading to study drug discontinuation were prepared. Treatment-emergent AEs were also summarized by maximum severity and by quartile of number of doses taken.

Vital signs at each visit, ECG at Screening, and physical examination findings at Screening and any unfavorable changes at the Final Visit were summarized by treatment and listed. Clinical laboratory values and change from baseline at each visit were summarized by treatment group using descriptive statistics. Shifts in laboratory values from Baseline to post-baseline (most abnormal value from any post-baseline sample) were tabulated. A separate listing was created of clinically significant laboratory abnormalities.

Results:

Overview:

Baseline demographics were similar between Study A and Study B groups. Approximately 82% of patients had OA and 6% had RA. The cumulative observed incidence of GUs over 6 mos was significantly lower in the PN400 groups versus the EC-naproxen groups (P<0.001 for both studies) (See Table 2). Of the 854 subjects in Study A+Study B, 201 were concomitant LDA users; the incidence of GUs in concomitant LDA users was lower in the PN400 group versus the EC-naproxen group [3.0% vs 28.4%, respectively, P<0.001] (See Table 3). Of the 201 concomitant LDA users out of the 854 total subjects in Study A+Study B, the incidence of GDUs in concomitant LDA users was lower in the PN400 group versus the EC-naproxen group [4.0% vs 32.4%, respectively, P<0.001] (See Table 4). The incidence of GUs in non-LDA users (n=653) across Study A+Study B subjects (n=854) was lower in the PN400 group versus the EC-naproxen group [6.4% vs 22.2%, P<0.001] (See Table 5). A pooled analysis of Study A and Study B demonstrated PN400 was associated with a significantly lower incidence of GU versus EC-naproxen regardless of age. (See Table 6). The relative risk reduction (RRR) for GUs in patients treated with PN400 was 64.9% (95% confidence interval [CI] 39.0, 79.8) in patients aged 50-59 yrs and 89.2% (95% CI 75.6, 95.3) in patients aged ≥60 yrs.

While the overall incidence of adverse events (AEs), treatment-related AEs, and SAEs was similar among treatment groups, pre-specified UGI AEs, including dyspepsia (See Table 9 for list of UGI AEs), occurred less frequently in the PN400 group. Indeed, patients treated with PN400 reported significantly improved SODA scores in all 3 patient domains after 6 months of treatment with PN400 versus EC-naproxen (See Table 8). For example, on the pain intensity domain of SODA questionnaire, PN400 patients showed significantly more improvement than EC-naproxen patients as early as the 1-month visit. The difference in LS means increased at each subsequent visit, with LS mean pain scores at 6-month (with last observation carried forward) in Study A of −5.51 in PN400 group and −0.15 points in EC-naproxen group (p<0.001) and in Study B of −2.64 in PN400 group and 0.09 points in EC-naproxen group (p=0.004). In the case of SODA pain intensity and non-pain intensity, a negative value for LS mean change implies improvement. In the case of SODA satisfaction, a positive value for LS mean change implies improvement.

PN400 was also associated with significantly higher rates of heartburn resolution and greater response in the OTE-DP scale for PN400 versus EC-naproxen (See Table 8). In the OTE-DP questionnaire, subjects in the PN400 group showed significantly more improvement than subjects in the EC-naproxen group, with a higher percentage of "better" response and a lower percentage of "worse" response in the PN400 group. Resolution of heartburn at each post-baseline visit was defined as a severity rating of "None" on the heartburn questionnaire. Only subjects with heartburn severity at baseline and post-baseline were included in the analysis. The comparison between treatment groups at each time point was made using a CMH test taking into account baseline severity stratified by LDA use at baseline. Table 10 presents the heartburn resolution by baseline symptom severity and by visit. From an early time point (month 1), PN400 treatment demonstrated a significantly higher resolution rate than EC-naproxen. The difference in heartburn resolution was consistent throughout the study period.

Based on a preliminary assessment of pooled data correlated between OTE-DP and SODA, the changes from baseline in SODA scores for PN400 were clinically relevant. An analysis of tolerability revealed fewer patients discontinued due to pre-specified UGI AEs/DUs in the PN400 group versus EC-naproxen group (Study A: 3.2% PN400 vs 12% EC-Naproxen, p<0.001; Study B: 4.8% PN400 vs 11.0% EC-naproxen, p=0.009) (See Table 7). The discontinuation rate due to any AE (including DU) was significantly lower in the PN400 group versus EC-naproxen group (Study A: 7% PN400 vs 16% EC-naproxen, p=0.004; Study B: 11% PN400 vs 18% EC-naproxen, p=0.029).

PN400 is associated with significantly improved UGI tolerability, as measured by Patient Reported Outcomes (PROs) and discontinuation rates due to NSAID-associated UGI AEs/DUs, compared with EC-naproxen. PN400 may provide a treatment option for at-risk patients to impart longer NSAID utilization patterns when GI intolerability is controlled.

Discussion:

This study demonstrates a clinically meaningful reduction in the occurrence of GUs in subjects taking PN400 versus EC-naproxen throughout 6 months of bid treatment in subjects requiring chronic NSAID treatment and who are at risk for NSAID-associated ulcers. The difference was apparent as early as 1 month into therapy and persisted throughout the study. PN400 treatment also resulted in a significantly lower incidence of DUs than EC-naproxen throughout 6 months of treatment.

Minimization of gastric side effects is of particular importance in chronic NSAID users who also take LDA for cardiovascular prophylaxis. The study results show that the benefit of PN400 over EC-naproxen was maintained in subjects who also took LDA.

PN400 was also better tolerated than EC-naproxen as demonstrated by decreased incidence of pre-specified NSAID associated UGI AEs, increased proportion of heartburn resolution, fewer discontinuations due to UGI AEs or DUs, improvement in patient reported outcomes as measured by SODA and OTE-DP.

PN400 was generally safe and well-tolerated. Overall AE rates were similar between the treatment groups. GI AE rates were lower among PN400 treated subjects compared to EC-naproxen treated subjects. This difference was primarily due to the difference in UGI AEs. While the mean duration of treatment for PN400 was longer than for EC-naproxen, the incidence of AEs did not increase with increased duration of exposure. An improved safety and tolerability profile of PN400 was also demonstrated by a higher proportion of subjects on PN400 (71%) completing 6 months of treatment without developing: (i) a GU or DU than subjects on EC-naproxen (42%), or (ii) a GU than subjects on EC-naproxen (48%).

Based on the results of this study, PN400 significantly reduced the incidence of both GUs and/or DUs and provided a better UGI safety profile than EC-naproxen. As such, PN400 appears to be a safe and well-tolerated treatment option for subjects at risk for NSAID-associated GUs and/or DUs.

Summary:

The results of these studies demonstrated that bid treatment with PN400 compared to EC-naproxen alone throughout 6 months in subjects at risk for NSAID-associated ulcers resulted in the following:

- The cumulative observed incidence of gastric ulcers throughout 1, 3 and 6 months was lower with PN 400 compared to EC-naproxen alone;
- A significantly lower proportion of subjects with NSAID-associated GU(s) in subjects with and without concomitant LDA;
- A significantly lower proportion of subjects with at least one pre-specified NSAID-associated UGI AE or DU;
- A significantly lower proportion of subjects discontinuing due to any pre-specified NSAID-associated UGI AE or DU;
- A significantly lower proportion of subjects with NSAID-associated DUs;
- A trend of a lower proportion of subjects with GUs regardless of LDA use, ulcer history, age<60 and ≥60 years, gender, race or ethnicity;
- A significantly higher proportion of subjects with heartburn resolution;
- A significantly better overall treatment effect on dyspepsia as measured by OTE-DP;
- Significantly improved dyspepsia symptoms as measured by SODA domains of pain, non-pain symptoms and subject satisfaction; and
- A significantly lower proportion of subjects discontinuing treatment due to an AE or DU.

TABLE 2

Cumulative Observed Data at 1, 3 and 6 Months in ITT Population

| | | GUs | | DUs | | UGI AEs and/or DUs | |
|---|---|---|---|---|---|---|---|
| | | No. (%) (95% CI) | p-value[1] | No. (%) (95% CI) | p-value[1] | No. (%) (95% CI) | p-value[1] |
| Study A 0-1 month | PN400 (n = 218) | 3 (1.4) (0.3-4.0) | <0.001 | 1 (0.5) (0.0-2.5) | 0.010 | | |
| | EC-naproxen (n = 216) | 28 (13.0) (8.8-18.2) | | 9 (4.2) (1.9-7.8) | | | |
| Study A 0-3 months | PN400 (n = 218) | 4 (1.8) (0.5-4.6) | <0.001 | 1 (0.5) (0.0-2.5) | 0.003 | | |
| | EC-naproxen (n = 216) | 42 (19.4) (14.4-25.4) | | 11 (5.1) (2.6-8.9) | | | |
| Study A 0-6 months | PN400 (n = 218) | 9 (4.1) (1.9-7.7) | <0.001 | 1 (0.5) (0.0-2.5) | 0.003 | 114 (52.3) (45.4-59.1) | <0.001 |
| | EC-naproxen (n = 216) | 50 (23.1) (17.7-29.4) | | 11 (5.1) (2.6-8.9) | | 149 (69) (62.4-75.1) | |
| Study B 0-1 months | PN400 (n = 210) | 4 (1.9) (0.5-4.8) | <0.001 | 2 (1.0) (0.1-3.4) | 0.168 | | |
| | EC-naproxen (n = 210) | 21 (10.0) (6.3-14.9) | | 6 (2.9) (1.1-6.1) | | | |
| Study B 0-3 months | PN400 (n = 210) | 10 (4.8) (2.3-8.6) | <0.001 | 2 (1.0) (0.1-3.4) | 0.013 | | |
| | EC-naproxen (n = 210) | 37 (17.6) (12.7-23.5) | | 11 (5.2) (2.6-9.2) | | | |
| Study B 0-6 months | PN400 (n = 210) | 15 (7.1) (4.1-11.5) | <0.001 | 2 (1.0) (0.1-3.4) | 0.007 | 114 (54.3) (47.3-61.2) | <0.001 |
| | EC-naproxen (n = 210) | 51 (24.3) (18.6-30.7) | | 12 (5.7) (3.0-9.8) | | 151 (71.9) (65.3-77.9) | |
| Study A + Study B 0-6 months | PN400 (n = 428) | 24 (5.6) (3.6-8.2) | — | 3 (0.7) (0.1-2.0) | <0.001 | 228 (53.3) (48.4-58.1) | <0.001 |
| | EC-naproxen (n = 426) | 101 (23.7) (19.7-28) | | 23 (5.4) (3.5-8.0) | | 300 (70.4) (65.8-74.7) | |

[1]p-Value for ulcer occurrence is from a CMH test stratified by low-dose aspirin use, at randomization.

TABLE 3

Cumulative Observed Incidence of GUs for LDA Users at 1, 3 and 6 Months in ITT Population

| | | GUs | |
|---|---|---|---|
| | | No. (%) (95% CI) | p-value |
| Study A 0-1 month | PN400 (n = 53) | 0 (0.0-6.7) | — |
| | EC-naproxen (n = 51) | 6 (11.8) (4.4-23.9) | |
| Study A 0-3 months | PN400 (n = 53) | 0 (0.0-6.7) | — |
| | EC-naproxen (n = 51) | 10 (19.6) (9.8-33.1) | |
| Study A 0-6 months | PN400 (n = 53) | 1 (1.9) (0.0-10.1) | — |
| | EC-naproxen (n = 51) | 12 (23.5) (12.8-37.5) | |
| Study B 0-1 month | PN400 (n = 46) | 0 (0.0-7.7) | — |
| | EC-naproxen (n = 51) | 10 (19.6) (9.8-33.1) | |
| Study B 0-3 months | PN400 (n = 46) | 0 (0.0-7.7) | — |
| | EC-naproxen (n = 51) | 14 (27.5) (15.9-41.7) | |

TABLE 3-continued

Cumulative Observed Incidence of GUs for LDA
Users at 1, 3 and 6 Months in ITT Population

|  |  | GUs No. (%) (95% CI) | p-value |
|---|---|---|---|
| Study B 0-6 months | PN400 (n = 46) | 2 (4.3) (0.5-14.8) | — |
|  | EC-naproxen (n = 51) | 17 (33.3) (20.8-47.9) |  |
| Study A + Study B 0-6 months | PN400 (n = 99) | 3 (3.0) (0.6-8.6) | P < 0.001 |
|  | EC-naproxen (n = 102) | 29 (28.4) (19.9-38.2) |  |

TABLE 4

Cumulative Observed Incidence of GDUs for
LDA Users at 6 Months in ITT Population

|  |  | GDUs No. (%) (95% CI) | p-value |
|---|---|---|---|
| Study A | PN400 (n = 53) | 1 (1.9) (0.0-10.1) | — |
|  | EC-naproxen (n = 51) | 14 (27.5) (15.9-41.7) |  |
| Study B | PN400 (n = 46) | 3 (6.5) (1.4-17.9) | — |
|  | EC-naproxen (n = 51) | 19 (37.3) (24.1-51.9) |  |
| Study A + Study B | PN400 (n = 99) | 4 (4.0) (1.1-10.0) | P < 0.001 |
|  | EC-naproxen (n = 102) | 33 (32.4) (23.4-42.3) |  |

TABLE 5

Incidence of GUs for Non-LDA Users at
1, 3 and 6 Months in ITT Population

|  |  | GUs No. (%) (95% CI) | p-value |
|---|---|---|---|
| Study A 0-1 month | PN400 (n = 165) | 3 (1.8) (0.4-5.2) | — |
|  | EC-naproxen (n = 165) | 22 (13.3) (8.5-19.5) |  |
| Study A 0-3 months | PN400 (n = 165) | 4 (2.4) (0.7-6.1) | — |
|  | EC-naproxen (n = 165) | 32 (19.4) (13.7-26.3) |  |
| Study A 0-6 months | PN400 (n = 165) | 8 (4.8) (2.1-9.3) | — |
|  | EC-naproxen (n = 165) | 38 (23.0) (16.8-30.2) |  |
| Study B 0-1 month | PN400 (n = 164) | 4 (2.4) (0.7-6.1) | — |
|  | EC-naproxen (n = 159) | 11 (6.9) (3.5-12.0) |  |
| Study B 0-3 months | PN400 (n = 164) | 10 (6.1) (3.0-10.9) | — |
|  | EC-naproxen (n = 159) | 23 (14.5) (9.4-20.9) |  |
| Study B 0-6 months | PN400 (n = 164) | 13 (7.9) (4.3-13.2) | — |
|  | EC-naproxen (n = 159) | 34 (21.4) (15.3-28.6) |  |

TABLE 5-continued

Incidence of GUs for Non-LDA Users at
1, 3 and 6 Months in ITT Population

|  |  | GUs No. (%) (95% CI) | p-value |
|---|---|---|---|
| Study A + Study B 0-6 months | PN400 (n = 329) | 21 (6.4) (4.0-9.6) | <0.001 |
|  | EC-naproxen (n = 324) | 72 (22.2) (17.8-27.7) |  |

TABLE 6

Pooled Cumulative Incidence of GUs in
Patients Aged <60 or ≥60 yrs

| Age (yrs) | PN400 | EC-naproxen | RRR (95% CI) | P |
|---|---|---|---|---|
| <60 | 18/216 (8.3) | 46/217 (21.2) | 60.7% (34.4, 76.4) | <0.001 |
| 50-59 | 15/202 (7.4) | 44/208 (21.2) | 64.9% (39.0, 79.8) | <0.001 |
| ≥60 | 6/212 (2.8) | 55/209 (26.3) | 89.2% (75.6, 95.3) | <0.001 |
| 60-69 | 6/157 (3.8) | 40/142 (28.2) | 86.4% (69.0, 94.1) | <0.001 |
| ≥70 | 0/55 (0.0) | 15/67 (22.4) | 100% | <0.001 |

*Cochran-Mantel-Haenszel test comparing GU rate

TABLE 7

Subjects Discontinuing from Study Due to Any Pre-Specified
NSAID-Associated UGI AE or DU in ITT Population

|  |  | UGI AE and/or DU that led to discontinuation No. (%) (95% CI) | p-value |
|---|---|---|---|
| Study A | PN400 (n = 218) | 7 (3.2) (1.3-6.5) | <0.001 |
|  | EC-naproxen (n = 216) | 26 (12) (8.0-17.1) |  |
| Study B | PN400 (n = 210) | 10 (4.8) (2.3-8.6) | 0.009 |
|  | EC-naproxen (n = 210) | 25 (11.9) (7.9-17.1) |  |
| Study A + Study B | PN400 (n = 428) | 17 (4.0) (2.3-6.3) | <0.001 |
|  | EC-naproxen (n = 426) | 51 (12.0) (9.0-15.4) |  |

TABLE 8

SODA, OTE-DP, And Heartburn Data After 6 mo of Treatment With PN400 vs. EC-naproxen

| Secondary end points | Study A | | | Study B | | |
|---|---|---|---|---|---|---|
| | PN400 (n = 218) | EC-naproxen (n = 216) | p-value | PN400 (n = 218) | EC-naproxen (n = 216) | p-value |
| SODA pain intensity, change from baseline | −5.51 | −0.15 | <0.001 | −2.64 | 0.09 | 0.004 |
| SODA non-pain symptoms, change from baseline | −2.16 | −0.47 | <0.001 | −1.11 | 0.11 | <0.001 |
| SODA satisfaction domain, change from baseline | 3.35 | 0.87 | <0.001 | 1.88 | 0.47 | 0.003 |
| OTE-DP, improvement since start of treatment n (%) | 93/204 (45.6) | 52/187 (27.8) | <0.001 | 79/184 (42.9) | 63/183 (34.4) | 0.017 |
| Resolution of heartburn, n (%) | 140/177 (79.1) | 65/115 (56.5) | <0.001 | 102/141 (72.3) | 62/121 (51.2) | <0.001 |

| Secondary end points | PN400 (n = 428) | EC-naproxen (n = 426) | p-value |
|---|---|---|---|
| SODA pain intensity, change from baseline | −4.14 | −0.06 | <0.001 |
| SODA non-pain symptoms, change from baseline | −1.65 | −0.19 | <0.001 |
| SODA satisfaction domain, change from baseline | 2.65 | 0.69 | <0.001 |
| OTE-DP, improvement since start of treatment n (%) | 172/388 (44.3) | 115/370 (31.1) | <0.001 |
| Resolution of heartburn, n (%) | 242/318 (76.1) | 127/236 (53.8) | <0.001 |

TABLE 9

List of Pre-Specified NSAID-Associated UGI AEs
Preferred Term

| | | |
|---|---|---|
| Gastritis | Gastrointestinal erosion | Abdominal tenderness |
| Erosive gastritis | Esophageal hemorrhage | Abdominal discomfort |
| Esophagitis | Gastric hemorrhage | Abdominal pain |
| Duodenitis | Duodenal hemorrhage | Esophageal discomfort |
| Esophageal stenosis | Gastric mucosal lesion | Esophageal disorder |
| Esophageal ulcer | Duodenal scarring | Gastroesophageal reflux disease |
| Reflux esophagitis | Gastritis hemorrhagic | Stomach discomfort |
| Erosive duodenitis | Gastrointestinal mucosal disorder | Vomiting |
| Erosive esophagitis | Abdominal pain, upper | Gastroesophagitis |
| Hyperchlorhydria | Dyspepsia | Epigastric discomfort |
| Gastrointestinal hemorrhage | Nausea | Duodenal ulcer hemorrhage |
| Varices esophageal | Duodenitis hemorrhagic | — |

TABLE 10

Resolution of Heartburn by Baseline Severity and Visit in ITT Population

| | | Study A | | | Study B | | |
|---|---|---|---|---|---|---|---|
| Month | Baseline Severity | PN400 N (%) | NAP N (%) | p-value | PN400 N (%) | NAP N (%) | p-value |
| 1 | None | 65/78 (83%) | 58/94 (62%) | | 67/88 (76%) | 67/91 (74%) | |
| | Mild | 37/62 (60%) | 11/57 (19%) | | 25/49 (51%) | 18/58 (31%) | |
| | Moderate | 16/38 (42%) | 7/37 (19%) | | 17/34 (50%) | 3/30 (10%) | |
| | Severe | 9/17 (53%) | 1/5 (20%) | | 3/9 (33%) | 1/5 (20%) | |
| | Total | 127/195 (65.1%) | 77/193 (39.9%) | <0.001 | 112/180 (62.2%) | 89/184 (48.4%) | 0.003 |
| 3 | None | 72/80 (90%) | 50/75 (67%) | | 70/85 (82%) | 52/76 (68%) | |
| | Mild | 43/62 (69%) | 11/41 (27%) | | 22/48 (46%) | 11/43 (26%) | |

TABLE 10-continued

Resolution of Heartburn by Baseline Severity and Visit in ITT Population

| Month | Baseline Severity | Study A | | | Study B | | |
|---|---|---|---|---|---|---|---|
| | | PN400 N (%) | NAP N (%) | p-value | PN400 N (%) | NAP N (%) | p-value |
| | Moderate | 16/37 (43%) | 7/28 (25%) | | 18/28 (64%) | 6/29 (21%) | |
| | Severe | 13/18 (72%) | 1/5 (20%) | | 5/7 (71%) | 1/3 (33%) | |
| | Total | 144/197 (73.1%) | 69/149 (46.3%) | <0.001 | 115/168 (68.5%) | 70/151 (46.4%) | <0.001 |
| 6 | None | 66/71 (93%) | 44/59 (75%) | | 60/68 (88%) | 43/58 (74%) | |
| | Mild | 43/60 (72%) | 14/31 (45%) | | 19/40 (48%) | 13/39 (33%) | |
| | Moderate | 19/31 (61%) | 7/21 (33%) | | 21/28 (75%) | 4/21 (19%) | |
| | Severe | 12/15 (80%) | 0/4 (0%) | | 2/5 (40%) | 2/3 (67%) | |
| | Total | 140/177 (79.1%) | 65/115 (56%) | <0.001 | 102/141 (72.3%) | 62/121 (51.2%) | <0.001 |

Severity of Dyspepsia Assessment (SODA) Instrument:

The SODA instrument was completed at Baseline and at each subsequent study visit. The questionnaire is a self-administered, multi-dimensional measure of dyspepsia-related health. Dyspepsia and related GI symptoms, including burping/belching, heartburn, bloating, passing gas, sour taste, nausea and bad breath, are commonly reported by patients taking NSAIDs and significantly impact treatment effectiveness, cost and quality of life. To capture dyspepsia and related GI symptoms, the SODA instrument was developed and validated for use in NSAID patients. Concepts measured within the 3 scales that comprise the SODA instrument are dyspepsia pain intensity, non-pain symptoms, and satisfaction with dyspepsia-related health.

The SODA contains 17 questions and can be completed in 5 minutes. It uses a 7-day recall period for questions in the pain intensity and non-pain symptoms domains. The questions are phrased as, "during the past 7 days, on average . . . " or, "during the past 7 days, how intense was your worst . . . ". The satisfaction domain questions are phrased to ask respondents about how satisfied or dissatisfied they are about their "present level" of abdominal discomfort.

SODA scores at Baseline and each post-baseline visit and change from Baseline for the 3 subscales (pain intensity, non-pain symptom, and satisfaction) were tabulated by treatment group at 1, 3 and 6 months using descriptive statistics. The mean change from Baseline at each timepoint was compared between treatment groups using an ANCOVA model with treatment and LDA use (Yes/No) at randomization as main effects, and baseline score as a covariate. The least squares mean (LSM) for each treatment group and the difference of LSMs between treatment groups along with the 95% CIs were calculated. Only subjects with both baseline and post-baseline scores were included in the ANCOVA. For the last assessment date for SODA more than 10 days after the last dosing date of study drug, the SODA scores were excluded from the analysis of each subscale. The last-observation-carried-forward imputation approach was used.

Heartburn Assessment:

At Baseline and 1, 3 and 6 months during the treatment period subjects were asked the following question regarding heartburn symptoms within the 7 days prior to the visit:

Over the last 7 days, please rate your heartburn symptoms as none: no symptoms mild: awareness of symptom, but easily tolerated moderate: discomforting symptom sufficient to cause interference with normal activities (including sleep)

severe: incapacitating symptom, with inability to perform normal activities (including sleep)

Heartburn was defined as a burning feeling rising from the stomach or lower part of the chest towards the neck.

Heartburn resolution at each post-baseline visit was defined as a response of "none" for the heartburn severity question. The proportion of subjects with heartburn resolution was tabulated by baseline severity and treatment group at 1, 3, and 6 months. Treatment groups were compared using a CMH test stratified by baseline heartburn severity and LDA use (Yes/No) at randomization. If the number of subjects in a cell of cross-strata was too small, only the Baseline heartburn was stratified in the CMH test. Subjects with both Baseline and post-baseline responses were included in this analysis. For the last assessment date of heartburn more than 10 days after the last dosing date of study drug, the heartburn severity was excluded from the analysis of this endpoint.

Overall Treatment for Dyspepsia (OTE-DP):

The OTE-DP has been developed based on, and is considered a derivative work of, the Global Ratings of Change Questionnaire, which was originally developed at McMaster University. It consists of the question: "Since treatment started, has there been any change in your upper abdominal pain and/or discomfort?" Responses may be rated as "Better", "the Same", or "Worse". Follow-up questions are asked if the response is anything other than "the Same".

The OTE-DP takes approximately 2 minutes to complete and was administered at the time of the final SODA administration. Any subject who had an ulcer confirmed by endoscopy at Visits 4 or 5 could complete the assessment by phone with study staff within 48 hours following the visit. All subjects completing the 6-month visit were to complete the OTE-DP with all other assessments prior to the final endoscopy.

The percentage of subjects with each of the 3 possible responses ("Better", "Same", "Worse") on the OTE-DP questionnaire, along with the follow-up response on the "Better" and "Worse" rating, was tabulated by treatment group. The difference between treatment groups in the distribution of responses was analyzed using a modified Wilcoxon rank-sum (Van Elteren) test, stratified by LDA use (Yes/No) at randomization.

What is claimed is:

1. A method of reducing the incidence of NSAID-associated gastric ulcers in patients taking low dose aspirin who are at risk of developing such ulcers, wherein the method comprises administering to said patient in need thereof a pharmaceutical composition in unit dose form comprising:

(a) 20 mg of esomeprazole, or pharmaceutically acceptable salt thereof, in a form and route sufficient to raise the gastric pH of said patient to at least 3.5 upon administration of one or more of said unit dose forms, and (b) 500 mg of naproxen, or pharmaceutically acceptable salt thereof;

wherein said unit dose form provides for coordinated release of the esomeprazole and the naproxen, wherein at least a portion of said esomeprazole, or pharmaceutically acceptable salt thereof, is released independent of the pH of the surrounding medium, wherein the unit dosage form releases less than 10% of the naproxen or a pharmaceutically acceptable salt thereof after 2 hours when tested using the USP Paddle Method in 1000 ml of 0.1N HCl at 75 rpm at 37° C.+/−0.5° C., wherein said pharmaceutical composition in unit dose form reduces the incidence of NSAID-associated ulcers in said patient and wherein administration of the unit dose form is more effective at reducing the incidence of the NSAID-associated ulcers in patients taking LDA than in patients not taking LDA who are administered the unit dose form.

2. The method according to claim 1, wherein the risk is associated with chronic NSAID treatment.

3. The method according to claim 1, wherein said patient is treated for a disease or disorder selected from pain and inflammation.

4. The method according to claim 1, wherein said patient is treated for a disease or disorder selected from osteoarthritis, rheumatoid arthritis, ankylosing spondylitis, and a combination thereof.

5. The method according to claim 1, wherein said unit dose form is at least about 95% free of sodium bicarbonate.

6. The method according to claim 1, wherein said unit dose form begins to release said naproxen, or a pharmaceutically acceptable salt thereof, when the pH of the surrounding medium is at about 4.0 or greater.

7. The method according to claim 1, wherein said unit dose form begins to release said naproxen, or a pharmaceutically acceptable salt thereof, when the pH of the surrounding medium is at about 4.5 or greater.

8. A method of reducing the incidence of NSAID-associated gastric ulcers in patients taking low dose aspirin who are at risk of developing such ulcers, wherein the method comprises administering to the patient a pharmaceutical composition in unit dosage form suitable for oral administration comprising:

(a) 20 mg of esomeprazole or a pharmaceutically acceptable salt thereof, that is immediately soluble when the dosage form is placed in an aqueous medium, independent of pH, in an amount effective to raise the gastric pH of the patient to at least 3.5 upon administration of one or more of the unit dosage forms, and (b) 500 mg of naproxen or pharmaceutically acceptable salt thereof, wherein the unit dosage form releases less than 10% of the naproxen or a pharmaceutically acceptable salt thereof after 2 hours when tested using the USP Paddle Method in 1000 ml of 0.1N HCl at 75 rpm at 37° C.+/−0.5° C.;

wherein said pharmaceutical composition in unit dose form reduces the incidence of NSAID-related ulcers in said patient and wherein administration of the unit dose form is more effective at reducing the incidence of the NSAID-associated ulcers in patients taking LDA than in patients not taking LDA who are administered the unit dose form.

9. The method of claim 8, wherein the risk is associated with chronic NSAID treatment.

10. The method of claim 8, wherein the patient is treated for a disease or disorder selected from pain, inflammation, osteoarthritis, rheumatoid arthritis, ankylosing spondylitis, and combinations thereof.

11. The method of claim 8, wherein the pharmaceutical composition is formulated to be administered to a patient twice daily.

12. The method according to claim 8, wherein the unit dosage form further comprises a pharmacologically inert, water soluble coating or film.

13. The method of claim 12, wherein the inert coating or film comprises a water soluble sugar.

14. The method of claim 8, wherein administration of the unit dosage form is more effective at reducing the risk of ulcer than treatment with enteric coated naproxen or a pharmaceutically acceptable salt thereof.

15. A method of reducing the incidence of NSAID-associated gastric ulcers in patients taking low dose aspirin (LDA) who are at risk of developing such ulcers, wherein the method comprises administering to said patient in need thereof twice a day for 1 month a pharmaceutical composition in unit dose form comprising:

(a) 20 mg of esomeprazole, or pharmaceutically acceptable salt thereof, in a form and route sufficient to raise the gastric pH of said patient to at least 3.5 upon administration of one or more of said unit dose forms, and (b) 500 mg of naproxen, or pharmaceutically acceptable salt thereof;

wherein said unit dose form provides for coordinated release of the esomeprazole and the naproxen, wherein at least a portion of said esomeprazole, or pharmaceutically acceptable salt thereof, is released independent of the pH of the surrounding medium, wherein the unit dosage form releases less than 10% of the naproxen or a pharmaceutically acceptable salt thereof after 2 hours when tested using the USP Paddle Method in 1000 ml of 0.1N HCl at 75 rpm at 37° C.+/−0.5° C., and wherein administration of the unit dose form is more effective at reducing the incidence of the NSAID-associated gastric ulcers in patients taking LDA than in patients not taking LDA who are administered the unit dose form.

16. A method of reducing the incidence of NSAID-associated gastric ulcers in patients taking low dose aspirin (LDA) who are at risk of developing such ulcers, wherein the method comprises administering to said patient in need thereof twice a day for 3 months a pharmaceutical composition in unit dose form comprising:

(a) 20 mg of esomeprazole, or pharmaceutically acceptable salt thereof, in a form and route sufficient to raise the gastric pH of said patient to at least 3.5 upon administration of one or more of said unit dose forms, and (b) 500 mg of naproxen, or pharmaceutically acceptable salt thereof;

wherein said unit dose form provides for coordinated release of the esomeprazole and the naproxen such that:

wherein at least a portion of said esomeprazole, or pharmaceutically acceptable salt thereof, is released independent of the pH of the surrounding medium, wherein the unit dosage form releases less than 10% of the naproxen or a pharmaceutically acceptable salt thereof after 2 hours when tested using the USP Paddle Method in 1000 ml of 0.1N HCl at 75 rpm at 37° C.+/−0.5° C., and wherein administration of the unit dose form is more effective at reducing the incidence of said ulcers in patients taking LDA than in patients not taking LDA who are administered the unit dose form.

* * * * *